United States Patent
Burkhart et al.

(10) Patent No.: US 11,464,505 B2
(45) Date of Patent: *Oct. 11, 2022

(54) SOFT SUTURE-BASED ANCHORS

(71) Applicant: ARTHREX, INC., Naples, FL (US)

(72) Inventors: Stephen S. Burkhart, Boerne, TX (US); Peter J. Dreyfuss, Naples, FL (US); Paul C. Brady, Knoxville, TN (US)

(73) Assignee: ARTHREX, INC., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/124,008

(22) Filed: Dec. 16, 2020

(65) Prior Publication Data

US 2021/0100544 A1    Apr. 8, 2021

Related U.S. Application Data

(63) Continuation of application No. 16/788,637, filed on Feb. 12, 2020, now Pat. No. 11,116,491, which is a continuation of application No. 15/242,331, filed on Aug. 19, 2016, now Pat. No. 10,595,845, which is a continuation of application No. 13/624,321, filed on Sep. 21, 2012, now Pat. No. 9,421,008.

(60) Provisional application No. 61/538,163, filed on Sep. 23, 2011.

(51) Int. Cl.
*A61B 17/04* (2006.01)
*A61B 17/06* (2006.01)

(52) U.S. Cl.
CPC .......... *A61B 17/04* (2013.01); *A61B 17/0401* (2013.01); *A61B 2017/0406* (2013.01); *A61B 2017/0409* (2013.01); *A61B 2017/0445* (2013.01); *A61B 2017/06185* (2013.01)

(58) Field of Classification Search
CPC ..... A61B 17/04; A61B 17/06; A61B 17/0401; A61B 17/0469; A61B 2017/0409; A61B 2017/0445; A61B 2017/06185; A61B 2017/06158
See application file for complete search history.

(56) References Cited

U.S. PATENT DOCUMENTS

| | | |
|---|---|---|
| 5,989,252 A | 11/1999 | Furnex |
| 6,296,659 B1 | 10/2001 | Foerster |
| 6,511,498 B1 | 1/2003 | Furnex |

(Continued)

FOREIGN PATENT DOCUMENTS

| | | |
|---|---|---|
| EP | 2 277 457 A1 | 1/2011 |
| WO | 2007005394 A1 | 1/2007 |
| WO | 2009/029914 A1 | 3/2009 |

OTHER PUBLICATIONS

R. Glousman et al., "JuggerKnow Sott Anchor," Biomet Sports Medicine, www.biometsportsmedicine.com/ 2010, 2011.

*Primary Examiner* — Vi X Nguyen
(74) *Attorney, Agent, or Firm* — Carlson, Gaskey & Olds, P.C.

(57) ABSTRACT

Suture constructs and methods for soft tissue to bone repairs. The suture construct is a soft, suture-based anchor which is self-cinching and has a specific, accordion-type configuration (i.e., with the ability to fold from a first, extended position to a second, folded or compressed position). The suture-based anchor may be formed essentially of a flexible material such as a high strength surgical suture, suture chain, or suture.

17 Claims, 34 Drawing Sheets

(56) References Cited

U.S. PATENT DOCUMENTS

| | | |
|---|---|---|
| 6,716,234 B2 | 4/2004 | Grafton et al. |
| 7,329,272 B2 | 2/2008 | Burkhart et al. |
| 7,803,173 B2 | 9/2010 | Burkhart et al. |
| 7,892,256 B2 | 2/2011 | Grafton et al. |
| 7,981,139 B2 | 7/2011 | Martin et al. |
| 8,118,836 B2 | 2/2012 | Denham et al. |
| 8,231,654 B2 | 7/2012 | Kaiser |
| 8,562,645 B2 | 10/2013 | Stone et al. |
| 8,652,171 B2 | 2/2014 | Stone |
| 8,652,172 B2 | 2/2014 | Denham |
| 8,795,334 B2 | 8/2014 | Astorino |
| 8,801,783 B2 | 8/2014 | Stone et al. |
| 8,986,327 B2 | 3/2015 | Karasic et al. |
| 9,078,651 B2 | 7/2015 | Astornio et al. |
| 9,370,352 B2 | 6/2016 | Astorino et al. |
| 2006/0184203 A1 | 8/2006 | Martin et al. |
| 2006/0259076 A1 | 11/2006 | Burkhart |
| 2007/0135843 A1 | 6/2007 | Burkhart |
| 2007/0185532 A1 | 8/2007 | Stone et al. |
| 2009/0306711 A1 | 12/2009 | Stone et al. |
| 2009/0318961 A1 | 12/2009 | Stone et al. |
| 2011/0022083 A1 | 1/2011 | DiMatteo |
| 2011/0098727 A1* | 4/2011 | Kaiser ................ A61B 17/0401 606/228 |
| 2011/0208239 A1 | 8/2011 | Stone et al. |
| 2011/0270278 A1 | 11/2011 | Overes et al. |
| 2012/0150203 A1 | 6/2012 | Brady et al. |
| 2014/0114330 A1 | 4/2014 | Karasic et al. |
| 2014/0277121 A1 | 9/2014 | Pilgeram et al. |
| 2015/0313586 A1* | 11/2015 | Burkhart ............... A61F 2/0805 606/232 |

\* cited by examiner

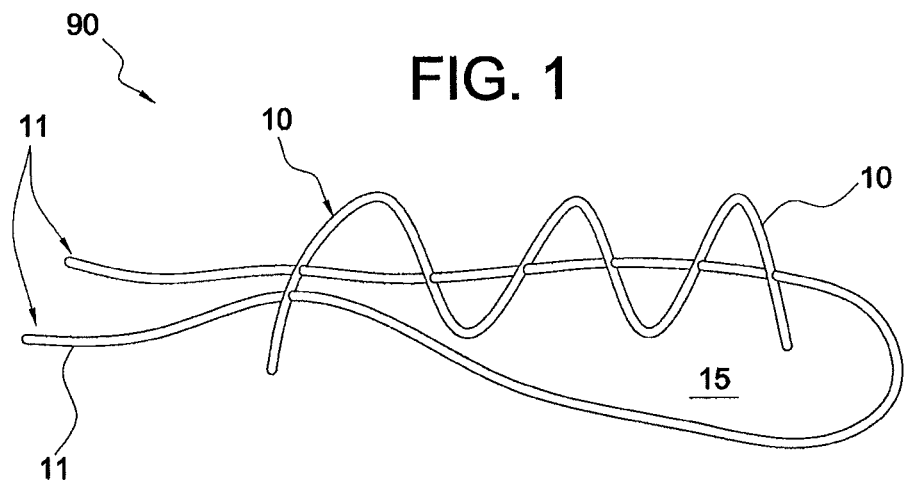
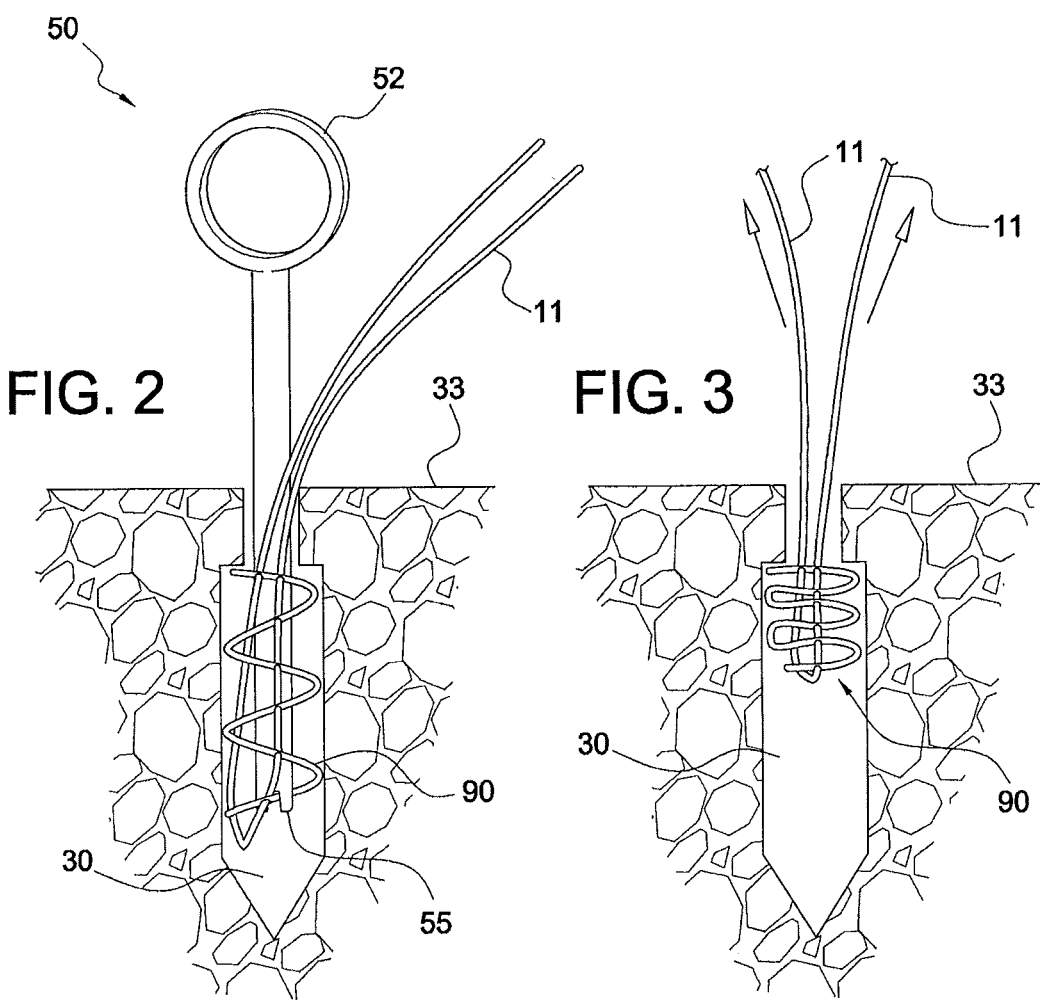

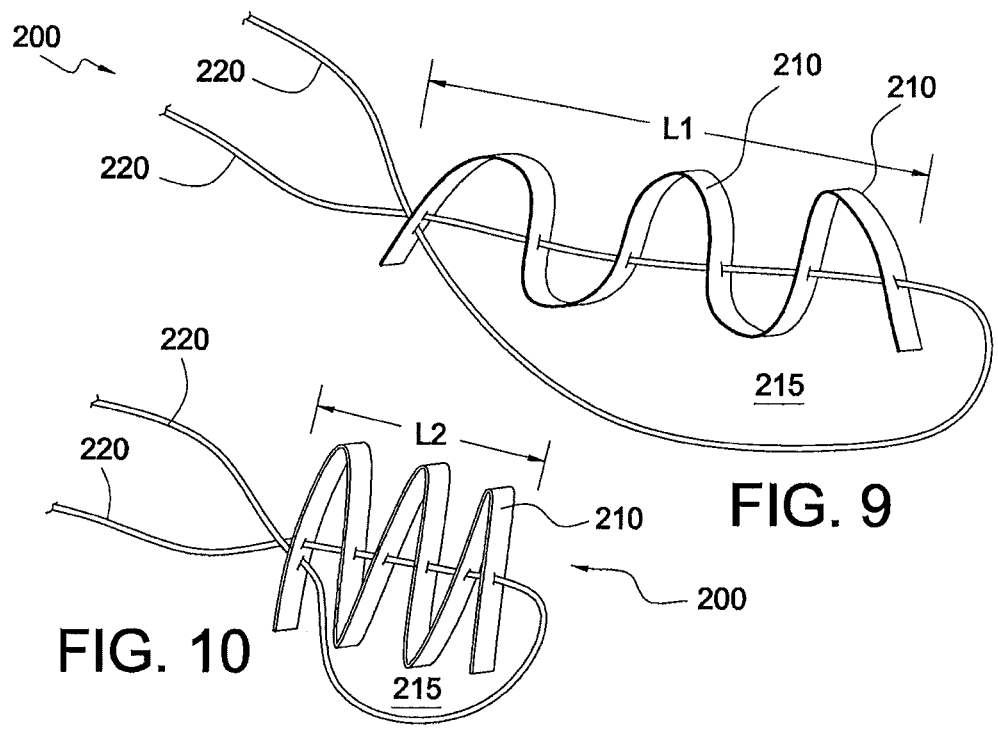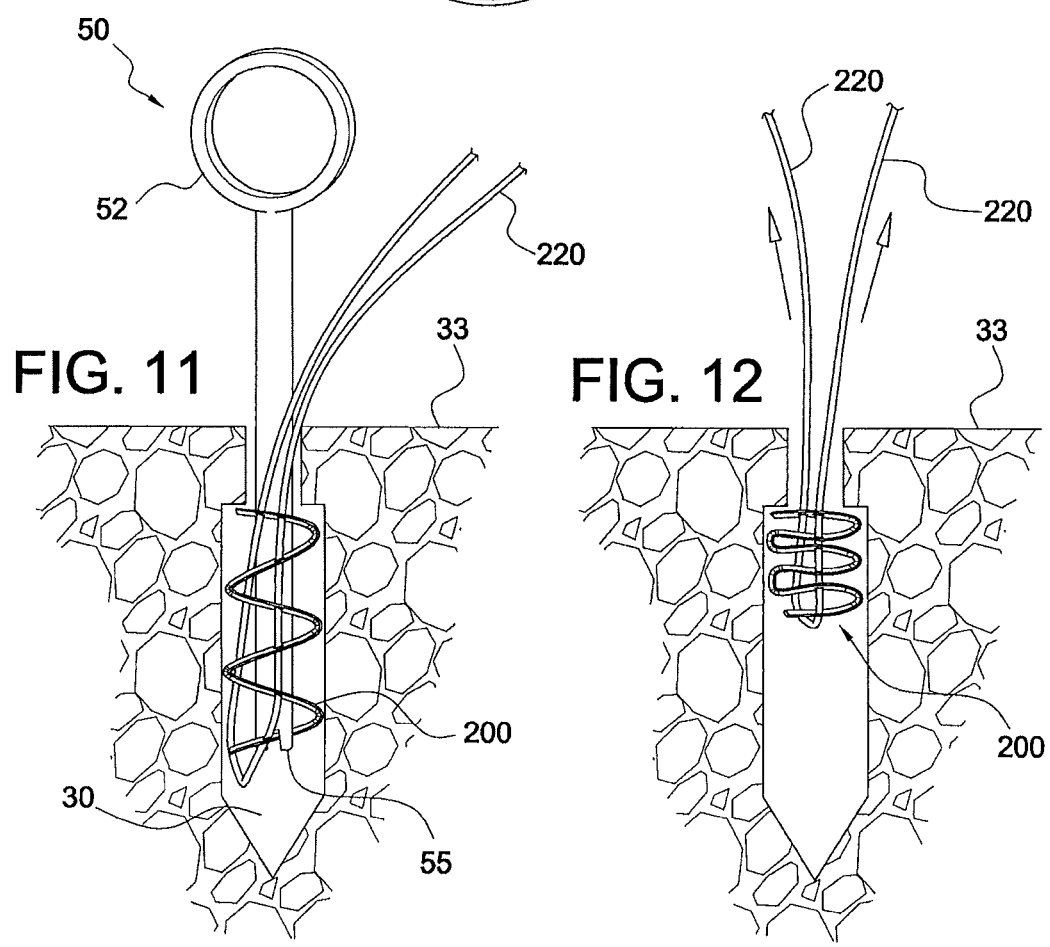

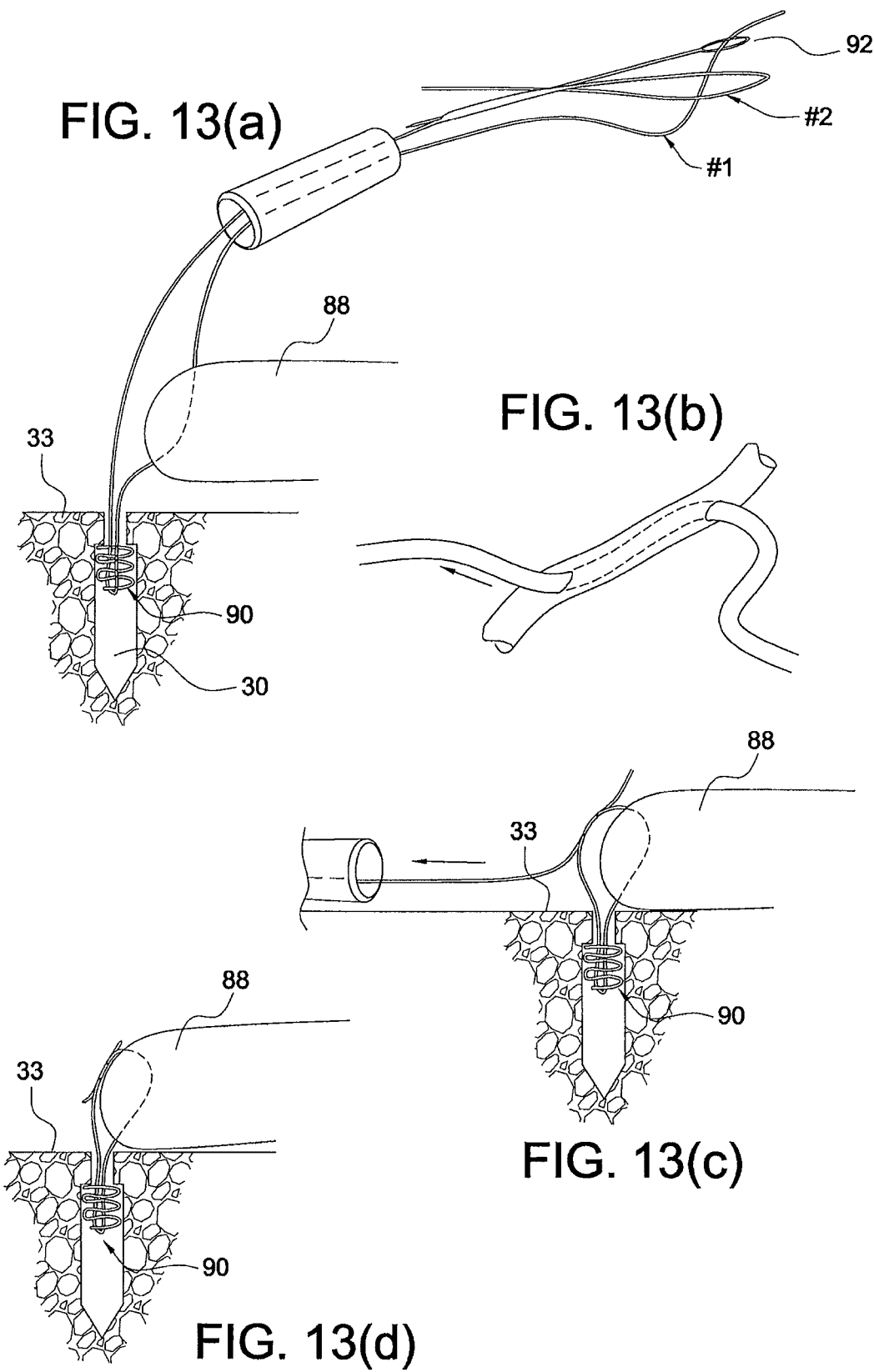

SOFT SUTURE-BASED ANCHORS

CROSS-REFERENCE TO RELATED APPLICATION

This is a continuation of U.S. patent application Ser. No. 16/788,637, filed Feb. 12, 2020, which is a continuation of U.S. patent application Ser. No. 15/242,331, filed Aug. 19, 2016 (now U.S. Pat. No. 10,595,845), which is a continuation of U.S. patent application Ser. No. 13/624,321, filed Sep. 21, 2012, (now U.S. Pat. No. 9,421,008), which claims the benefit of U.S. Provisional Application No. 61/538,163, filed Sep. 23, 2011, the disclosures of which are incorporated by reference in their entireties herein.

FIELD OF THE INVENTION

The present invention relates to the field of surgery and, more particularly, to a joint or ligament reconstruction technique and associated fixation and reconstruction device.

BACKGROUND

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided the bone tissue. Knotless suture anchors, such as the two piece Arthrex PushLock® anchor, disclosed in U.S. Pat. No. 7,329,272, have been developed to facilitate tissue fixation to bone.

It would be desirable to provide a suture construct which has a design that allows tensioning of the construct as necessary and upon insertion into bone. Also needed is a suture construct that may be knotless and that is formed essentially of a soft material such as suture (or suture-based materials or other soft materials and/or compositions) with the ability to be inserted into a bone socket and then tightened by simple traction on one of the suture strands.

SUMMARY

The present invention provides a suture construct for fixation of soft tissue to bone with the ability to tension/retension the suture construct. The suture construct may be a knotted or a knotless construct.

The suture construct of the present invention is a soft, suture-based anchor which is self-cinching and has a specific, accordion-type configuration (i.e., with the ability to fold from a first, extended position to a second, folded or compressed position). The suture-based anchor may be formed essentially of a flexible material such as suture (for example, FiberWire® suture) or suture chain (such as FiberChain®) or suture tape (such as FiberTape®), to form a SutureLock™ ChainLock™ or TapeLock™ suture-based anchor, respectively.

A suture (such as FiberWire®) may be employed to form a SutureLock™ anchor. Another suture (for example, a TigerWire® suture) is first passed through a length of the FiberWire® through multiple points such that the TigerWire® circles back to exit through the FiberWire® near the spot where it entered (in a suture-through-suture technique), creating a loop that penetrates the suture in a "sine-wave" configuration. Tensioning the two free ends of the TigerWire® tightens the loop and "accordionizes" the suture, creating expansion of the SutureLock™ anchor to create an interference fit. The SutureLock™ anchor is inserted into a bone socket/tunnel and the tails of the TigerWire® are tensioned to "accordionize" the FiberWire® (i.e., to fold or compress the FiberWire® to achieve an "accordion-like" shape). Additional sliding sutures may be added (threaded) through the soft anchor (SutureLock™ anchor) so that the soft anchor becomes double-loaded, triple-loaded, etc., i.e., multiple-loaded, as desired and depending on the specific characteristics of each surgical repair.

A suture chain (such as FiberChain® or FiberLink®) may be employed to form a ChainLock™ anchor. A free end of the suture chain (FiberChain®) is first passed through the chain (for example, through every other link in the chain) so that, when the free end is tightened, it collapses the chain in an accordion-like fashion with laterally-projecting links to produce an interference fit. The loop is closed down by pulling tension on the tail and this collapses the link like an accordion, forming the ChainLock™ anchor (i.e., folding or compressing the FiberChain® to achieve an "accordion-like" shape). A flexible strand (for example, a FiberWire®) is threaded through a middle link of the accordion. This flexible strand acts as the sliding suture for tissue fixation after the anchor is placed into bone. Once the ChainLock™ anchor is inserted into the bone socket/tunnel, the sliding suture (FiberWire®) is tensioned so that the tail of the FiberChain is flush with the bone after tensioning. Additional sliding sutures may be added (threaded) through the soft anchor (ChainLock™ anchor) so that the soft anchor becomes double-loaded, triple-loaded, etc., i.e., multiple-loaded, as desired and depending on the specific characteristics of each surgical repair.

A suture tape (such as FiberTape®) may be employed to form a TapeLock™ anchor. A FiberWire® suture is first passed through a length of the FiberTape® such that the FiberWire® circles back to exit through the FiberTape® near the spot where it entered, creating a loop that penetrates the tape in a "sine-wave" configuration. Tensioning the two free ends of the FiberWire® tightens the loop and "accordionizes" the suture tape (i.e., folding or compressing the FiberTape® to achieve an "accordion-like" shape), creating expansion of the TapeLock™ anchor to create an interference fit. The TapeLock™ anchor is inserted into a bone socket/tunnel and the tails of the FiberWire® are tensioned to "accordionize" the FiberTape® (i.e., to fold or compress the FiberTape® to achieve an "accordion-like" shape). Additional sliding sutures may be added (threaded) through the soft anchor (TapeLock™ anchor) so that the soft anchor becomes double-loaded, triple-loaded, etc., i.e., multiple-loaded, as desired and depending on the specific characteristics of each surgical repair.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 1 illustrates a suture-based anchor (SutureLock™ anchor) according to an exemplary embodiment of the present invention.

FIG. 2 illustrates the suture-based anchor (SutureLock™ anchor) of FIG. 1 secured in bone with a pusher (a ring-handed instrument).

FIG. 3 illustrates the suture-based anchor (SutureLock™ anchor) of FIG. 2 with at least one tail of the suture tensioned, to accordionize the suture-based anchor (Suture-Lock™ anchor), so that the suture is flush with the inner cortex of the bone after tensioning.

FIG. 9 illustrates a suture-based anchor (TapeLock™ anchor) according to yet another exemplary embodiment of the present invention (with a FiberWire® suture passed through the length of a suture tape).

FIG. 10 illustrates the suture-based anchor (TapeLock™ anchor) of FIG. 9 with the two free ends of the FiberWire® suture tightened to accordionize the suture tape.

FIG. 11 illustrates the suture-based anchor (TapeLock™ anchor) of FIG. 10 secured in bone with a pusher (a ring-handed instrument).

FIG. 12 illustrates the suture-based anchor (TapeLock anchor) of FIG. 11 with the tails of the FiberWire tensioned, to accordionize the suture-based anchor (TapeLock anchor) so that the suture tape is flush with the inner cortex of the bone after tensioning.

FIGS. 13(a)-(d) illustrate subsequent steps of a method of self-reinforcing knotless fixation of soft tissue with a suture-based anchor of the present invention, and according to an exemplary method of knotless fixation of the present invention.

DETAILED DESCRIPTION

Figure 4:
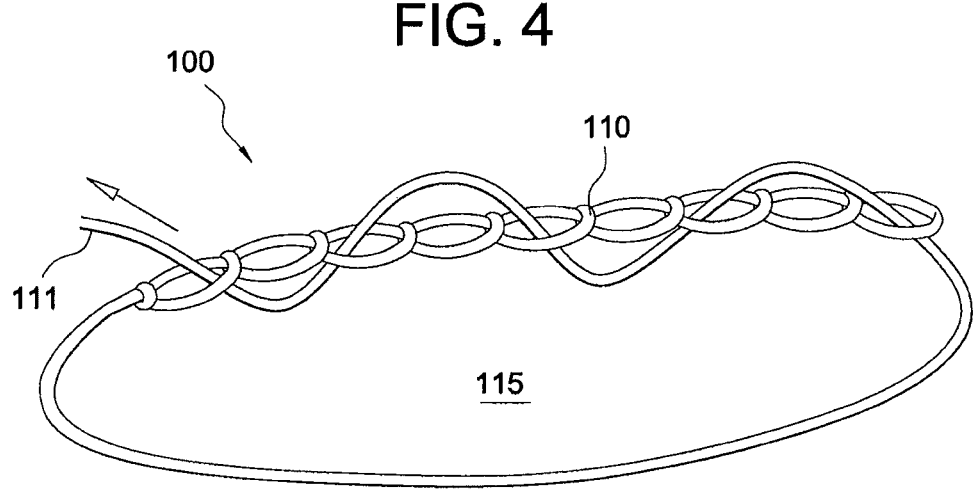
FIG. 4 illustrates a suture-based anchor (ChainLock™ anchor) according to another exemplary embodiment of the present invention.

The present invention provides surgical systems and methods for knotted or knotless soft tissue (ligament, tendon, graft, etc.) repair and fixation, such as fixation of soft tissue to bone. The suture anchor of the present invention is a suture-based anchor with a body that consists essentially of a flexible material such as suture, high-strength suture such as FiberWire® suture (disclosed in U.S. Pat. No. 6,716,234), suture tape such as FiberTape® (disclosed in U.S. Pat. No. 7,892,256), suture chain such as FiberChain® (disclosed in U.S. Pat. No. 7,803,173), among others, or combination of these materials. The body of the flexible material forms a loop that closes down and collapses the loop like an accordion. Once the suture anchor is placed into a bone socket or tunnel, tails of the anchor are tensioned to allow the loop of flexible material to "accordionize" and to create an interference fit.

Referring now to the drawings, where like elements are designated by like reference numerals, FIGS. 1-12 illustrate exemplary soft suture-based anchors 90, 100, 200 of the present invention that are provided with a specific, accordion-type configuration. The suture-based anchors 90, 100, 200 may be formed essentially of a flexible material such as suture (for example, FiberWire® suture) or suture chain (such as FiberChain®) or suture tape (such as FiberTape®), to form a SutureLock™, ChainLock™ or TapeLock™ suture-based anchor, respectively.

FIG. 1 illustrates suture-based anchor 90 (SutureLock™ anchor 90) formed essentially of a flexible strand 10 (for example, a suture such as a FiberWire® suture 10). Another flexible strand 11 (for example, another FiberWire® or TigerWire® suture 11) is passed through the length of the FiberWire® 10 (with a needle, for example) in a suture-through-suture technique. The flexible strand 11 (TigerWire® suture 11) is preferably a colored flexible strand or suture (or colored differently from the flexible strand 10) to allow easy differentiation between the strands and to allow medical personnel (e.g., surgeon) to distinguish between the sutures. The TigerWire® 11 circles back to exit through the FiberWire® 10 near the spot where it entered, creating a loop 15 that penetrates the suture in a "sine-wave" configuration. The flexible strand 11 (TigerWire® suture 11) may be passed through the suture 10 at different locations and as desired, for example, at predetermined insertion points on the length of the suture 10 (such as six locations, for example), which may be equally spaced from each other or from at least some of the remaining insertion points, or which may not be equally spaced relative to the other insertion points. The end of the TigerWire® suture 11 is brought back to reenter the FiberWire 10 near the spot where it first entered, to close the FiberWire® 10 and form closed loop 15.

When the two free ends of flexible strand 11 (TigerWire® suture 11) are tightened (as shown in FIGS. 2 and 3), the FiberWire® 10 is "accordionized" and the loop 15 collapses in an accordion-like fashion with laterally-projecting links to produce an interference fit. The loop 15 is closed down by pulling tension on the tails and this tension collapses the suture like an accordion, forming the SutureLock™ anchor 90.

Figure 8:
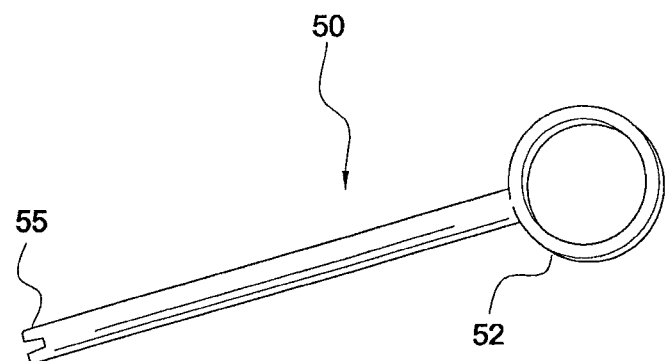
FIG. 8 is an enlarged view of the pusher (ring-handed instrument) of FIG. 6.

FIGS. 2 and 3 illustrate the insertion of the SutureLock™ anchor 90 into a bone socket/tunnel 30 employing a pusher 50 (a ring-handed instrument) provided with a ring 52 and a forked tip 55. Details of instrument 50 are shown in FIG. 8. Forked tip 55 of the pusher 50 is employed for pushing the SutureLock™ anchor 90 into the bone socket or tunnel 30 formed within bone 33 (i.e., pushing the FiberWire® suture 10 at an insertion point where the TigerWire® suture 11 entered the FiberWire® suture 10).

FIG. 3 illustrates the tails of the TigerWire® suture 11 tensioned, to "accordionize" the FiberWire® and secure the SutureLock™ anchor 90 within bone 33. The suture is flush with the bone 33 after tensioning.

Figure 5:
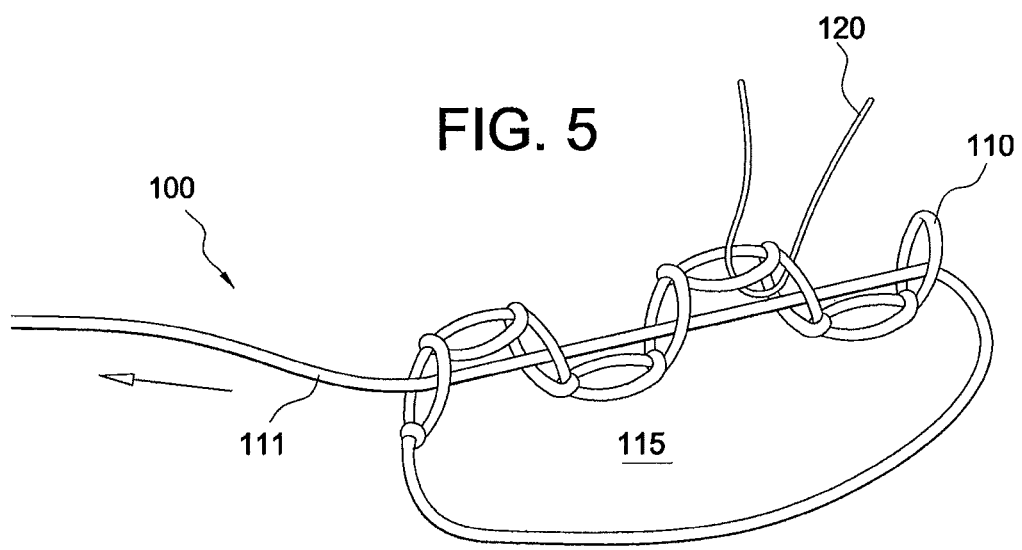
FIG. 5 illustrates the suture-based anchor (ChainLock™ anchor) of FIG. 4 with a FiberWire threaded through a middle link and with one tail of the suture chain tensioned.

FIG. 4 illustrates suture-based anchor 100 (ChainLock™ anchor 100) formed essentially of a suture chain 110 (such as FiberChain® or FiberLink™ 110) comprising a plurality of links having similar or different diameters and lengths. A free end 111 of the FiberChain® suture 110 is first passed through the chain to form a closed suture chain loop 115. In an exemplary embodiment only, the free end 111 is passed through every other link in the chain, with a graft preparation needle, for example. When the free end 111 is tightened (as shown in FIG. 5), the loop 115 collapses in an accordion-like fashion with laterally-projecting links to produce an interference fit. The loop 115 is closed down by pulling tension on the tail and this collapses the link like an accordion, forming the ChainLock™ anchor.

A flexible strand 120 (for example, a slide suture such as a FiberWire® suture or TigerWire® suture) is threaded through a middle link of the accordion. Strand 120 will act as the sliding suture for tissue fixation after the suture-based anchor 100 is placed into bone. Once the ChainLock™ anchor 100 is inserted into the bone socket/tunnel, the sliding suture 120 (FiberWire® suture) is tensioned so that the tail of the FiberChain® suture is flush with the bone after tensioning.

Figure 6:
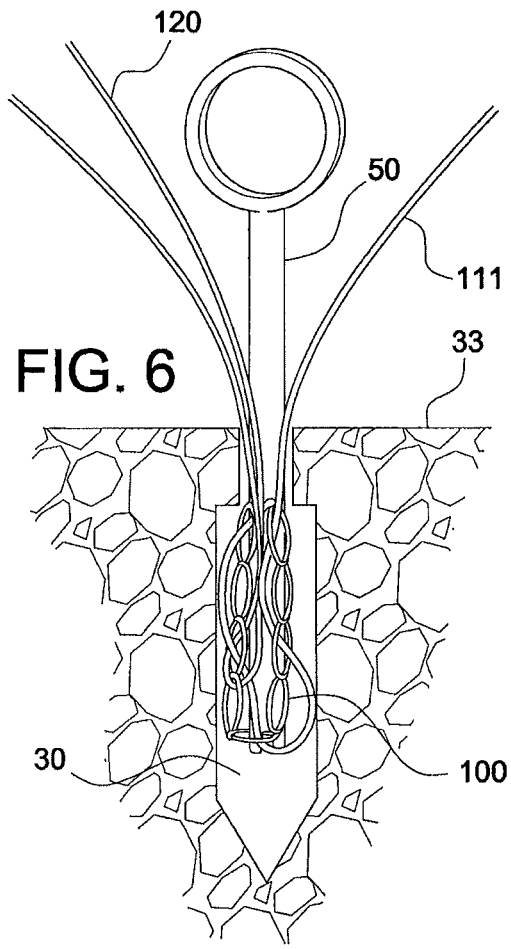
FIG. 6 illustrates the suture-based anchor (ChainLock™ anchor) of FIG. 5 secured in bone with a pusher (a ring-handed instrument).

FIG. 5 illustrates the suture-based anchor 100 (ChainLock™ anchor) with the sliding suture 120 (FiberWire® suture 120) threaded through a middle link and with one tail 111 of the suture chain 110 tensioned. FIG. 6 illustrates the suture-based anchor 100 (ChainLock™ anchor) inserted/pushed into bone socket or tunnel 30 with a pusher (a ring-handed instrument) 50 having a ring 52 and a tip 55. Details of instrument 50 are shown in FIG. 8. Forked tip 55 of the pusher 50 is employed for pushing the suture/FiberChain® into the bone socket or tunnel 30 formed within bone 33.

Figure 7:
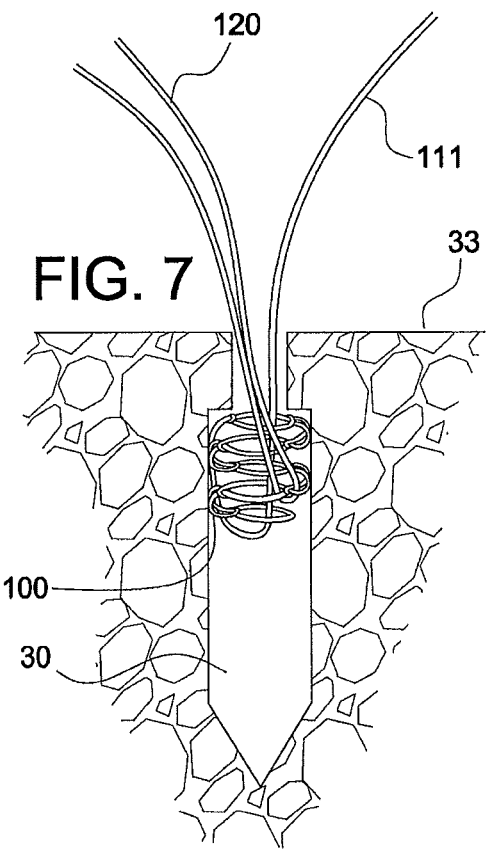
FIG. 7 illustrates the suture-based anchor (ChainLock™ anchor) of FIG. 6 with a tail of the suture chain tensioned, to accordionize the suture-based anchor (ChainLock™ anchor), so that the suture chain is flush with the inner cortex of the bone after tensioning.

FIG. 7 illustrates the suture-based anchor 100 (ChainLock™ anchor) with the tail of the suture chain 110 tensioned, to accordionize the suture-based anchor 100 (ChainLock™ anchor) and to tighten the circle/loop 115, so that the suture chain 110 is flush with the bone 33 after tensioning. The two tails of sliding suture 120 ensure tissue fixation after the suture-based anchor 100 is placed within the bone tunnel/socket 30.

FIGS. 9-12 illustrate a suture-based anchor (TapeLock™ anchor) 200 according to another exemplary embodiment of the present invention. Suture-based anchor 200 (TapeLock™ anchor 200) is formed essentially of a suture tape 210, such as, for example, a FiberTape® suture 210. Suture tape 210 has a first length L1, a width W and a thickness (now shown).

As illustrated in FIG. 9, flexible strand 220 (for example, a suture such as a FiberWire® or TigerWire® suture 220) is passed through a length of the FiberTape® 210 (with a needle, for example) such that the FiberWire® 220 circles back to exit through the FiberTape® 210 near the spot where it entered, creating a loop 215 that penetrates the tape in a "sine-wave" configuration. The flexible strand 220 (FiberWire® suture 220) may be passed through the tape 210 at different locations and as desired, for example, at predetermined insertion points on the length of the suture tape 210 (such as four locations, for example), which may be equally spaced from each other or from at least some of the remaining insertion points, or which may not be equally spaced relative to the other insertion points. The end of the TigerWire® suture 220 is brought back to reenter the FiberTape 210 near the spot where it first entered, to close the FiberTape® 210 and form closed loop 215.

FIG. 10 shows how the tensioning the two free ends of the FiberWire® suture 220 tightens the loop 215 and "accordionizes" the suture tape 210 (to achieve a length L2 smaller than the length L1), creating expansion of the TapeLock anchor 200 to create an interference fit (i.e., achieving expansion in a transversal orientation relative to the longitudinal axis of the bone tunnel/socket). The TapeLock™ anchor 200 is inserted into a bone socket/tunnel 30 (as shown in FIG. 11) employing a pusher 50 (a ring-handed instrument) provided with a ring 52 and a forked tip 55. Forked tip 55 of the pusher 50 is employed for pushing the TapeLock™ anchor 200 into the bone socket or tunnel 30 formed within bone 33 (i.e., pushing the FiberTape® 210 at an insertion point where the TigerWire® suture 220 entered the tape).

FIG. 12 illustrates the tails of the FiberWire® suture 220 tensioned, to "accordionize" the FiberTape® and secure the TapeLock™ anchor 200 within bone 33. The suture tape is flush with the bone 33 after tensioning. The TapeLock™ anchor 200 having the expanded/accordion shape (in the deployed or accordionized position) is captured below the cortical surface of the bone to achieve fixation within the bone socket/tunnel 30.

Although the suture-based anchors 90, 100, 200 have been described above with two free suture ends for tying knots, the suture-based anchors of the present invention could be also provided as knotless suture constructs. If a knotless suture construct is desired, a knotless embodiment may be created by splicing a coreless suture (for example, a coreless FiberWire® suture) on the end of the anchor. This coreless FiberWire 8 suture would have a mechanism similar to that of an Arthrex ACL Tightrope® (like a Chinese finger-trap). The coreless suture may be threaded back through, as detailed below with reference to FIGS. 13(a)-(d) and FIGS. 14(a)-(e), which depict subsequent steps of two methods of self-reinforcing knotless fixation of soft tissue with the soft anchors of the present invention (for example, the suture-based anchors) and according to two exemplary methods of knotless fixation of the present invention.

FIGS. 13(a)-(d): Soft suture anchor 90 is inserted into bone socket/tunnel 30 by employing pusher 50, for example. Suture anchor 90 is also provided with two limbs, limb #1 and limb #2, of which one limb (for example, limb #1) is passed through soft tissue 88. A threader 92 (for example, a flexible nitinol threader 92) is employed to thread limb #1 through about the center of limb #2 and for a predetermined length, for example, for about 5 mm (FIG. 13(a)). This will lock the suture by a finger-trap mechanism (FIG. 13(b)). The limb is pulled to tighten the loop (FIG. 13(c)). The suture is then cut close to the loop and the sutured tissue 88.

FIGS. 14(a)-(e): an alternative self-reinforcing knotless fixation with the suture-based anchors of the present invention. A suture is threaded through suture for about 4 mm, to form the double-looped construct with loop #1 (10 a) and loop #2 (10 b) shown in FIG. 14(a). Pull-cord #1 and pull-cord #2 extend between the saddle 15 of the loop assembly. The double-looped construct is similar to a finger-trap mechanism and is self-locking by pulling the two pull-cords.

Figure 14A:
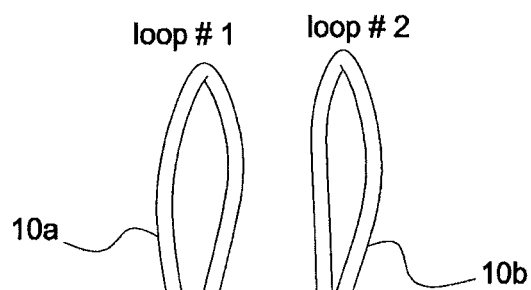
FIGS. 14(a)-(e) illustrate subsequent steps of another method of self-reinforcing knotless fixation of soft tissue with a suture-based anchor of the present invention, and according to another exemplary method of knotless fixation of the present invention.
Figure 14B:
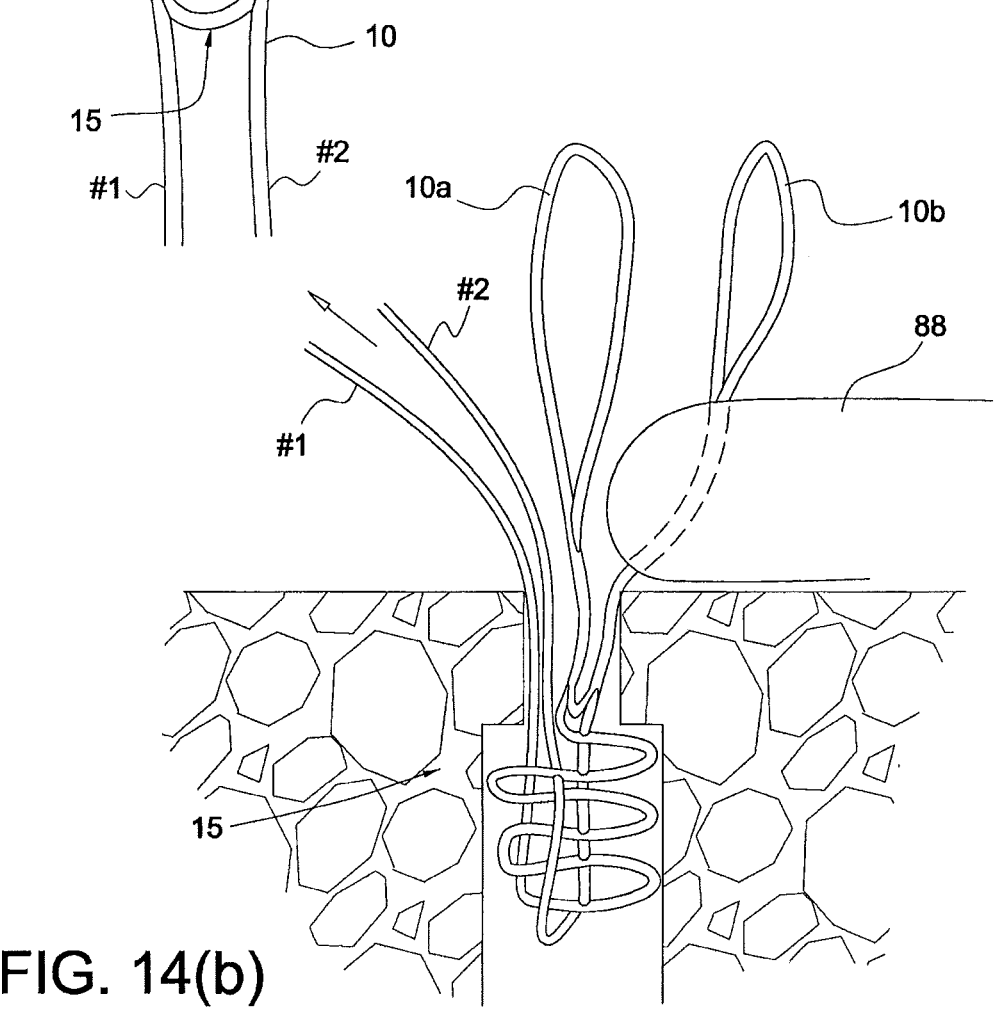

Loop #2 is shuttled through soft tissue 88 as shown in FIG. 14(b). By pulling on pull-cords #1 and #2, the saddle 15 of the loop assembly 10 a, 10 b is pre-positioned within one loop of the soft anchor's accordion.

Figure 14C:
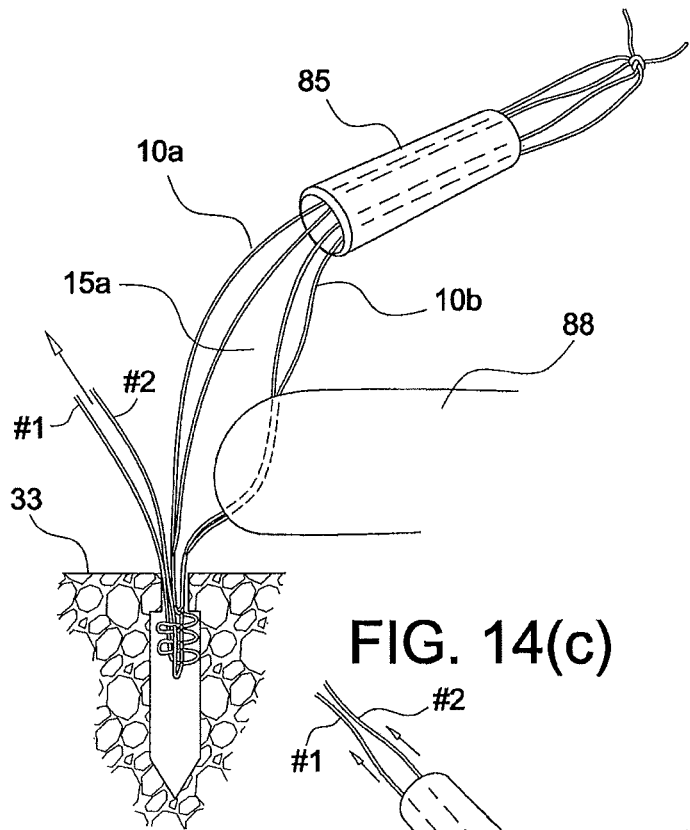
Figure 14D:
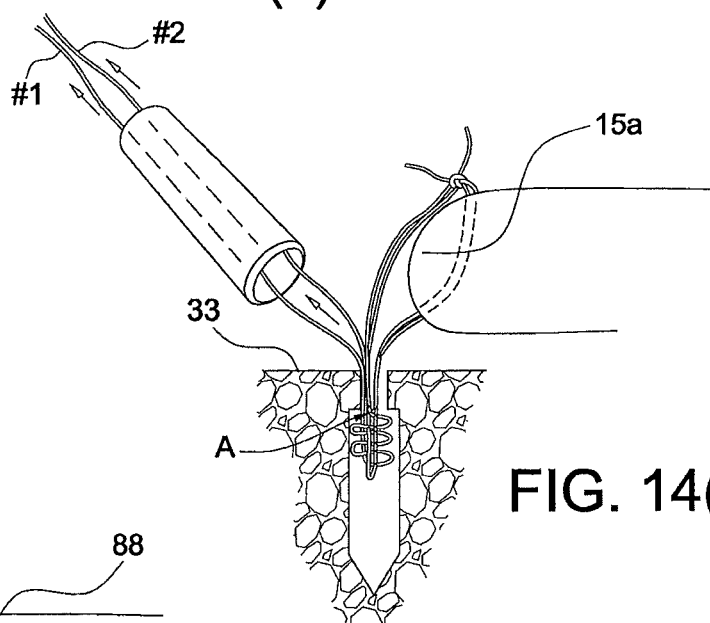
Figure 14E:
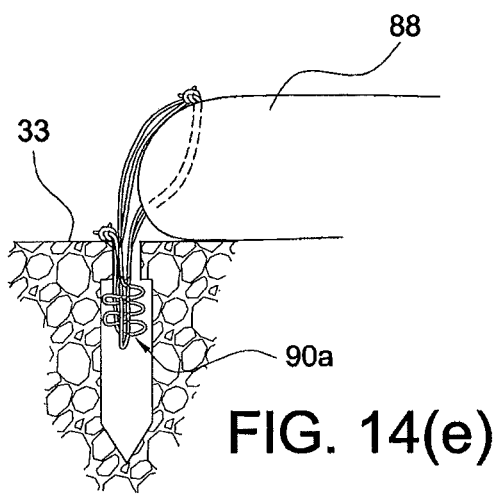

Outside of the working cannula 85, separate sutures are used to tie loop #1 (10 a) and loop #2 (10 b) together, to create closed loop down to the pull-cords (FIG. 14(c)). Subsequently, the pull-cords are pulled to bring the loops down tightly over the soft tissue 88. The self-locking and self-reinforcing finger-trap mechanism occurs at point A of FIG. 14(d). The construct is tightened by pulling on the pull-cords. FIG. 14(e) shows final knotless construct 90 a with the pull-cords cut flush with bone 33.

The flexible strands employed for the formation of the suture-based anchors 90, 100, 200, 90 a may be high-strength sutures, such as the high strength suture sold by Arthrex, Inc. of Naples, Fla. under the registered tradename TigerWire® or FiberWire®, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material. The preferred FiberWire® suture includes a core within a hollow braided construct, the core being a twisted yarn of UHMWPE.

The suture tape employed for the formation of suture anchor 200 may be a FiberTape® as disclosed in U.S. Pat. No. 7,892,256, the disclosure of which is herein incorporated by reference. The suture tapes may have the same, uniform width or may have different widths, and may comprise the same or different materials.

Although the terms "chain," "suture chain" and Fiber-Chain® have been used interchangeably in this application, it must be understood that the term "chain" is not limited to only "suture chain" or FiberChain® rather, the term "chain" encompasses a plurality of loops of any material and of any dimension (i.e., loops of similar or different diameters), as long as the loops are interconnected to each other. An exemplary suture chain that may be used in the present application is described in U.S. Pat. No. 7,803,173 and/or in U.S. Patent Appl. Publ. No. 2007/0135843, the disclosures of both of which are incorporated by reference in their entirety herewith.

The flexible material forming the suture anchors 90, 100, 200, 90 a may be also formed of suture tape or a combination of suture and tape, a stiff material, or combination of stiff and flexible materials, depending on the intended application.

Figure 15:
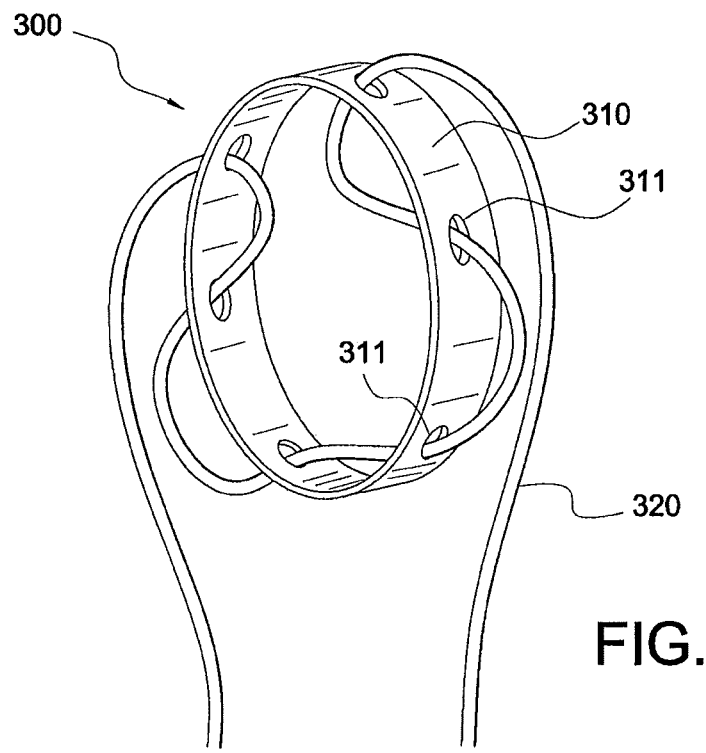
FIG. 15 illustrates a folding tube suture anchor according to another exemplary embodiment of the present invention.
Figure 16:
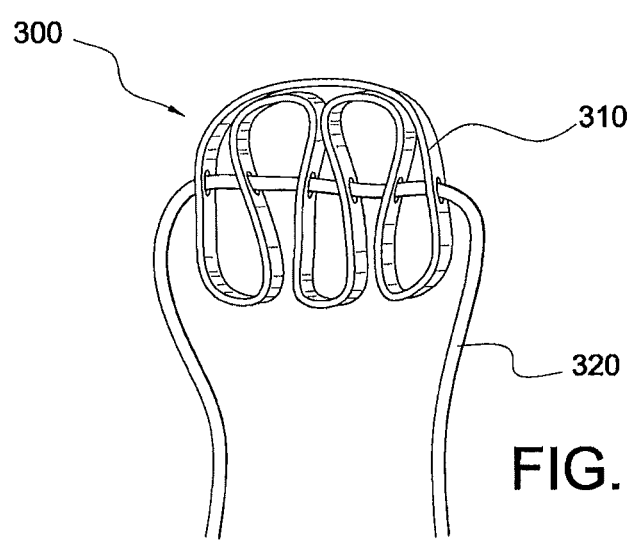
FIG. 16 illustrates the folding tube suture anchor of FIG. 15 tensioned.

FIGS. 15-21 illustrate another exemplary embodiment of a soft anchor 300 of the present invention. Anchor 300 is a folding tube suture anchor which may be formed of textile or homogenous material (no sheath) and which does not have any "hard" surfaces. As shown in FIGS. 15 and 16, folding tube suture anchor 300 is formed of a tube (cylinder) 310 provided with apertures/holes 311 to allow a flexible strand 320 to pass therethrough. When the tube is inserted into a bone tunnel/socket and when tension is applied, the tube 310 folds and lodges into the bone tunnel/socket. The distance between two adjacent apertures/holes 311 may be the same or different.

FIGS. 17-21 illustrate subsequent steps of folding the tube anchor 300 of FIG. 15.

Figure 17:
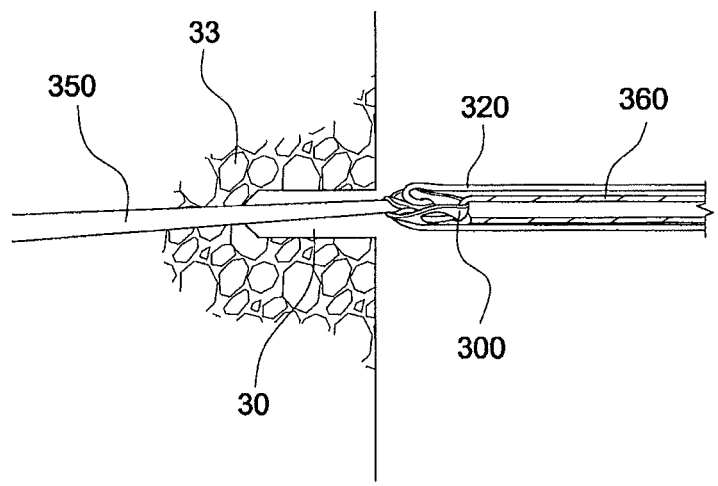
FIGS. 17-21 illustrate subsequent steps of folding the tube anchor of FIG. 15.

FIG. 17: Inserter 350 (pulling here just to be out of the way) and blue FiberWire® suture 320 in loaded position using TigerWire® suture 360 keep assembly tight and loaded, adjacent bone tunnel/socket 30 in bone 33.

Figure 18:
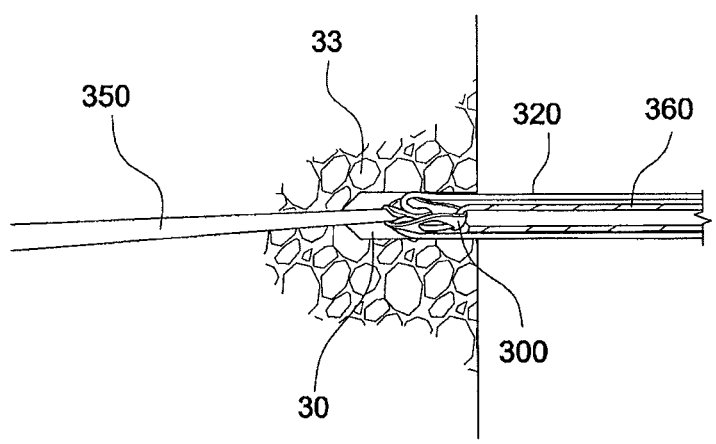

FIG. 18: Inserter 350 "pushes" the assembly 300 into the pilot hole (but only as deep as desired ending position).

Figure 19:
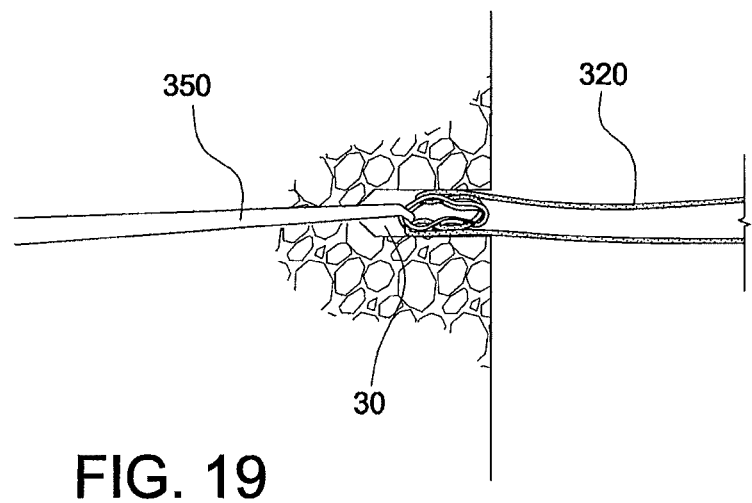

FIG. 19: The TigerWire® suture 360 is removed and the anchor 300 is ready to be deployed (inserter 350 is still "pushing" the anchor into the pilot hole).

Figure 20:
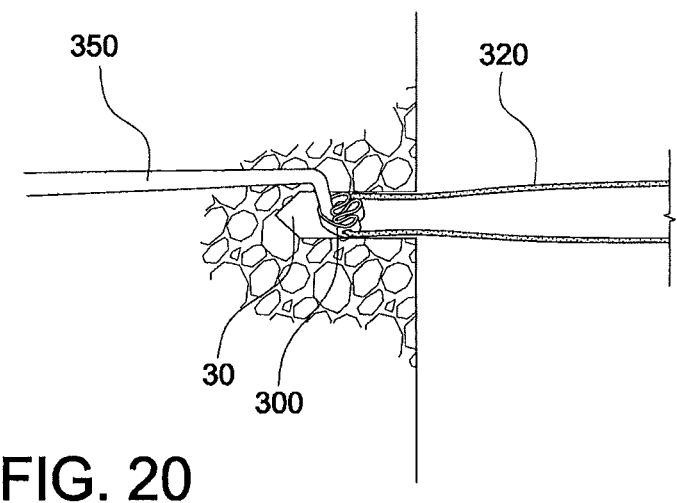

FIG. 20: The blue FiberWire® suture 320 is pulled (will slide just like a normal anchor) to create a "folding" effect (the inserter 350 is still "pushing" the anchor 300 into the pilot hole).

Figure 21:
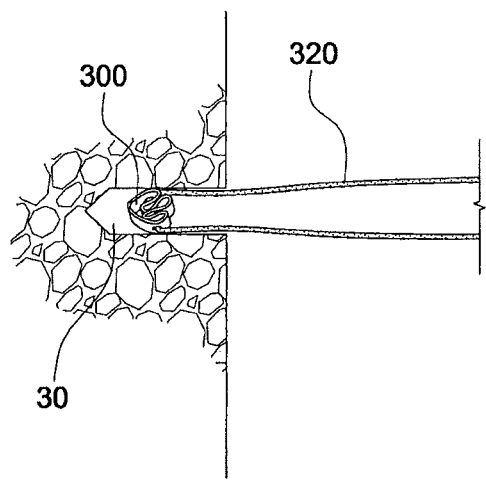

FIG. 21: Once the anchor 300 is folded, the inserter 350 is removed as the anchor 300 is fixed into place in bone tunnel/socket 30.

FIGS. 22-40 illustrate soft anchor implants 400 a, 400 b, 400 c (accordion anchors 400 a, 400 b, 400 c) for tissue repairs (for example, soft tissue repairs such as PASTA repairs (Partial Articular-Sided Tendon Avulsion repairs)) according to yet additional embodiments of the present invention. As detailed below, these soft anchor implants are smaller than the conventional bone anchors (which are relatively large) and are formed of a soft (suture-based) material (in contrast to the conventional anchors which are typically formed of hard materials such as PEEK, PLLA, bTCP, metal, PGA, biomaterials, etc.). The soft anchor implants 400 a, 400 b, 400 c detailed below may be employed in percutaneous insertions by simple surgical techniques, with multiple additional indications, to provide biomechanically strong constructs.

Figure 22:
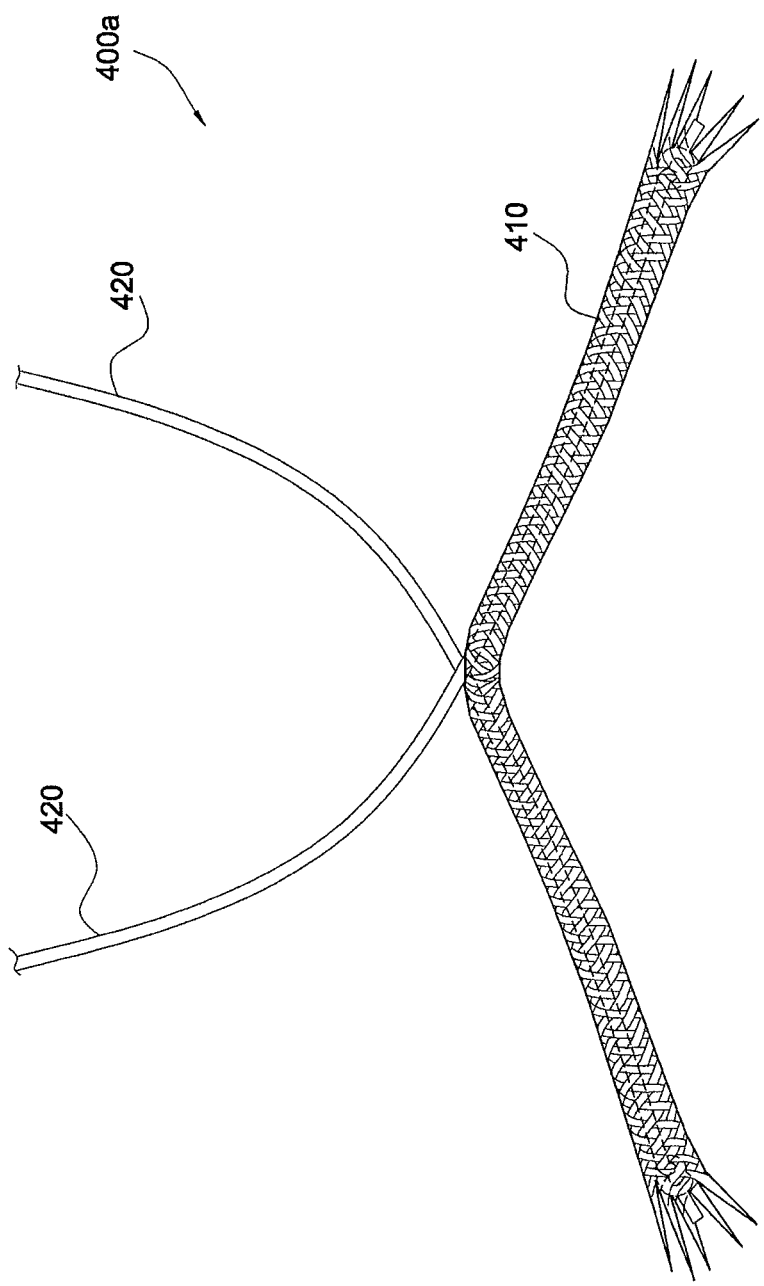
FIG. 22 illustrates a soft anchor implant for soft tissue repairs according to another embodiment of the present invention.
Figure 23:
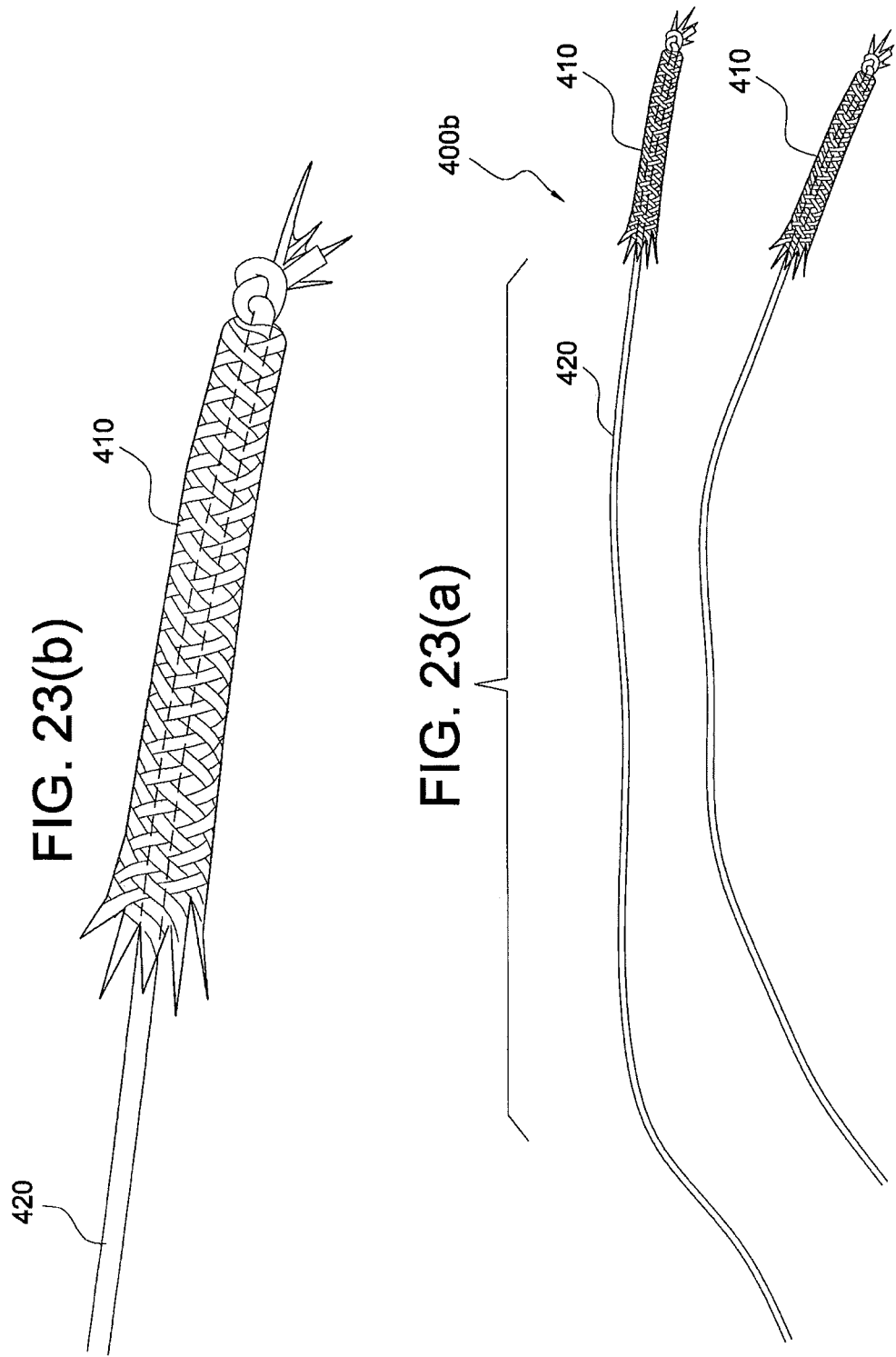
FIGS. 23(a) and (b) illustrate a soft anchor implant for soft tissue repairs according to another embodiment of the present invention.
Figure 24:
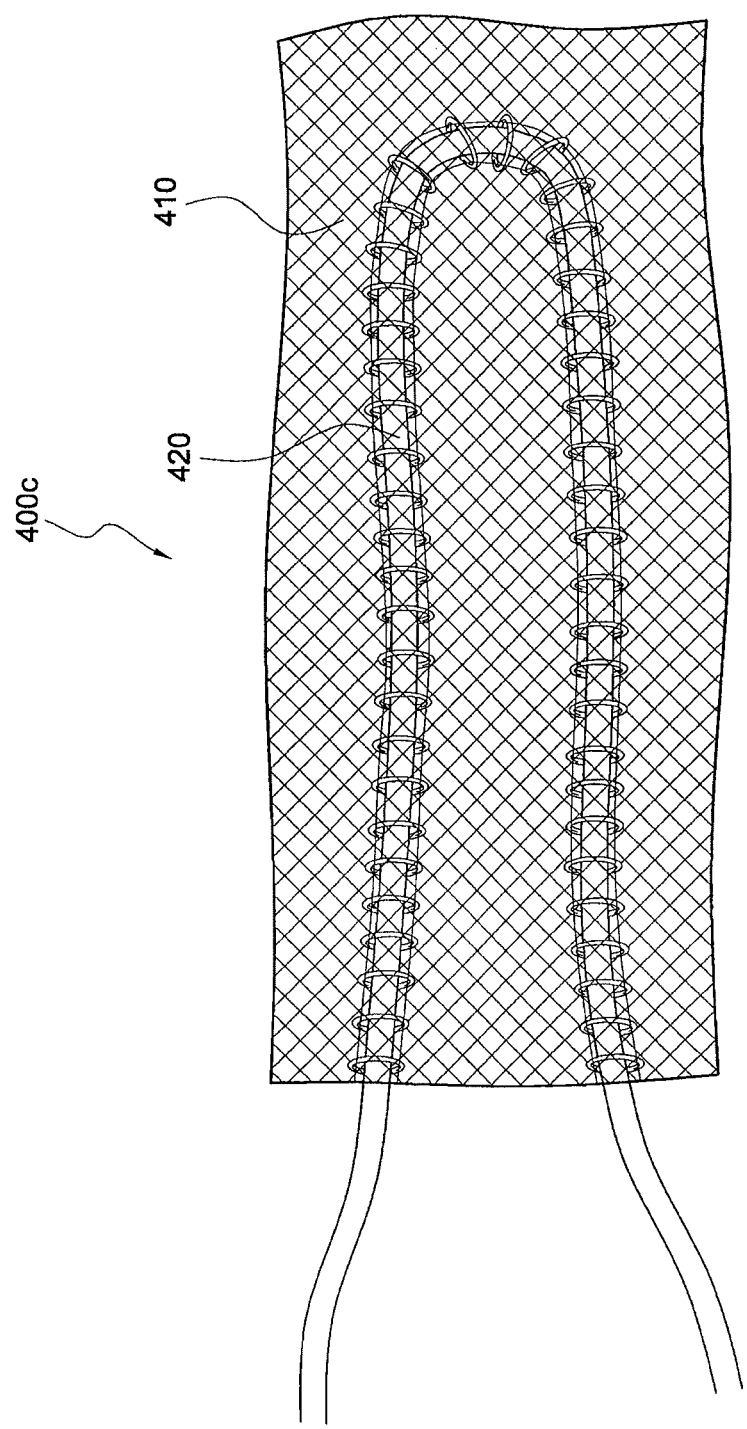
FIG. 24 illustrates a soft anchor implant for soft tissue repairs according to another embodiment of the present invention.

FIGS. 22-24 illustrate exemplary soft anchor implants 400 a (implant A), 400 b (implant B), 400 c (implant C), respectively, of the present invention. Soft anchor 400 a of FIG. 22 is a suture tape/core suture construct. Soft anchor 400 b of FIG. 23 is a two anchor construct. Soft anchor 400 c of FIG. 24 is a loop anchor construct.

Figure 25:
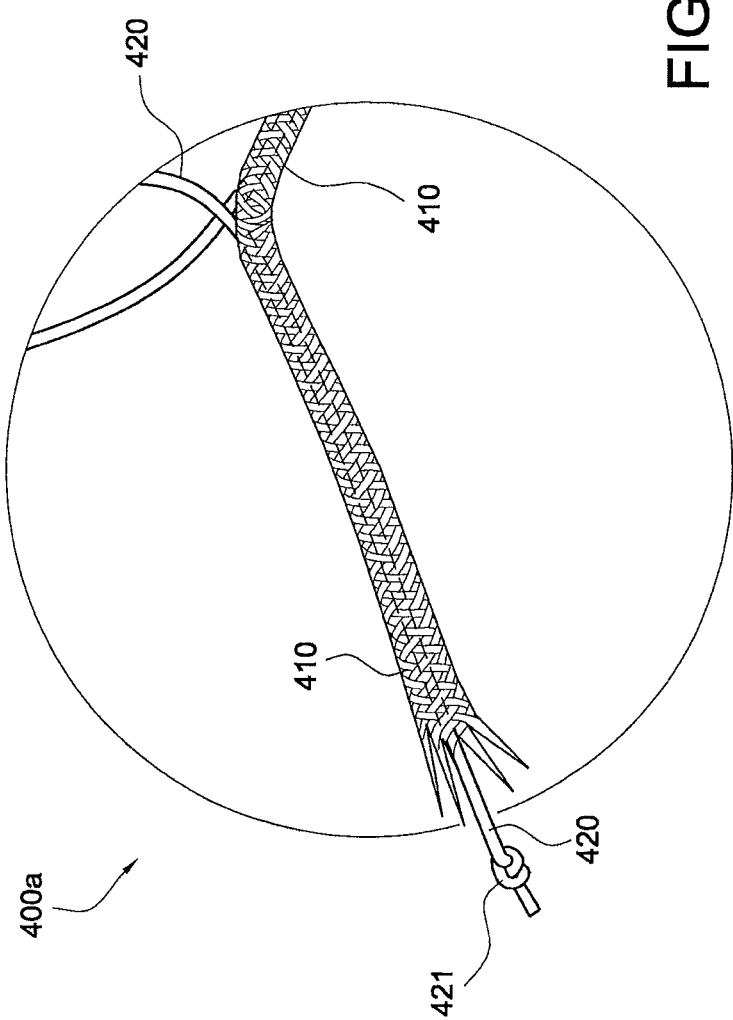
FIG. 25 illustrates a soft anchor implant for soft tissue repairs according to another embodiment of the present invention.

FIG. 25 illustrates soft anchor implant 400 a (implant A) formed of a suture tape 410 (for example, a FiberTape®) which has a length of flexible strand 420 (for example, a suture core such as a #2 FiberWire® core) incorporated therein (i.e., extending within the body of the suture tape or on the outside of the suture tape). A small knot 421 is tied at one end of the flexible strand 420 (and of the end of the tape 410) so that, when the suture core (FiberWire® core) 420 is pulled at the other end, the suture tape 410 bunches up (folds up) similarly to the bellows of an accordion. The bunched-up suture tape 410 becomes the soft anchor 400 a of the present invention.

As detailed below, implants 400 b and 400 c are similar to the implant 400 a in that they are also formed essentially of a suture tape (a FiberTape®) 410 with a flexible strand (a FiberWire® core) 420 incorporated through the suture tape (i.e., extending throughout the length of the suture tape and within the body of the suture tape, or secured on the outside of the suture tape).

Figure 26A:
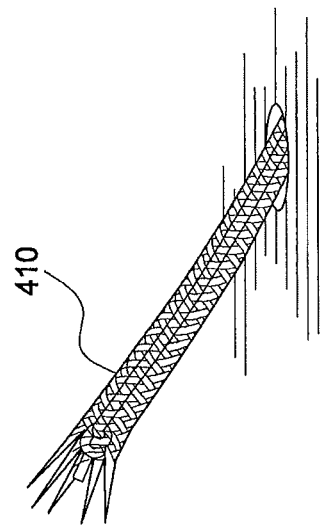
FIGS. 26(a)-(c) illustrate subsequent steps of forming the soft anchor implant of FIG. 22.
Figure 26B:
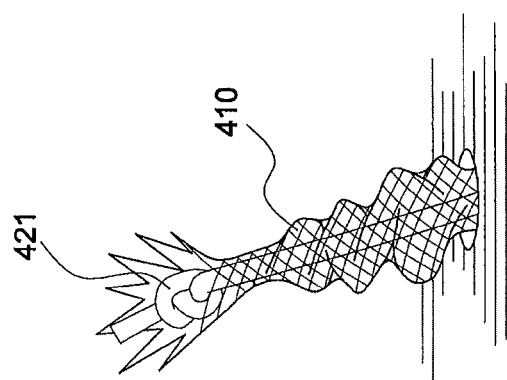
Figure 26C:
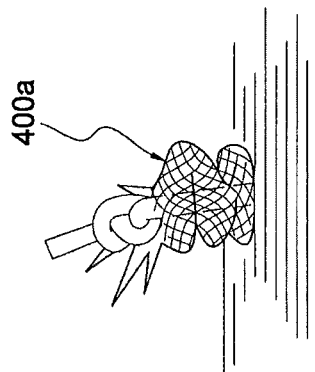

FIGS. 26(a)-(c) depict the formation of soft anchor implant 400 a (implant A). The implant is passed through an exemplary piece of cardboard. The core suture 420 of the implant is then pulled so that the knot 421 at the end of the tape 410 helps the suture tape 410 bunch up down to the cardboard. The tape will completely bunch up underneath the cardboard.

FIGS. 27-33(a) and (b) illustrate additional views of the soft anchor implant 400 a (implant A) and methods of tissue fixation.

Figure 27:
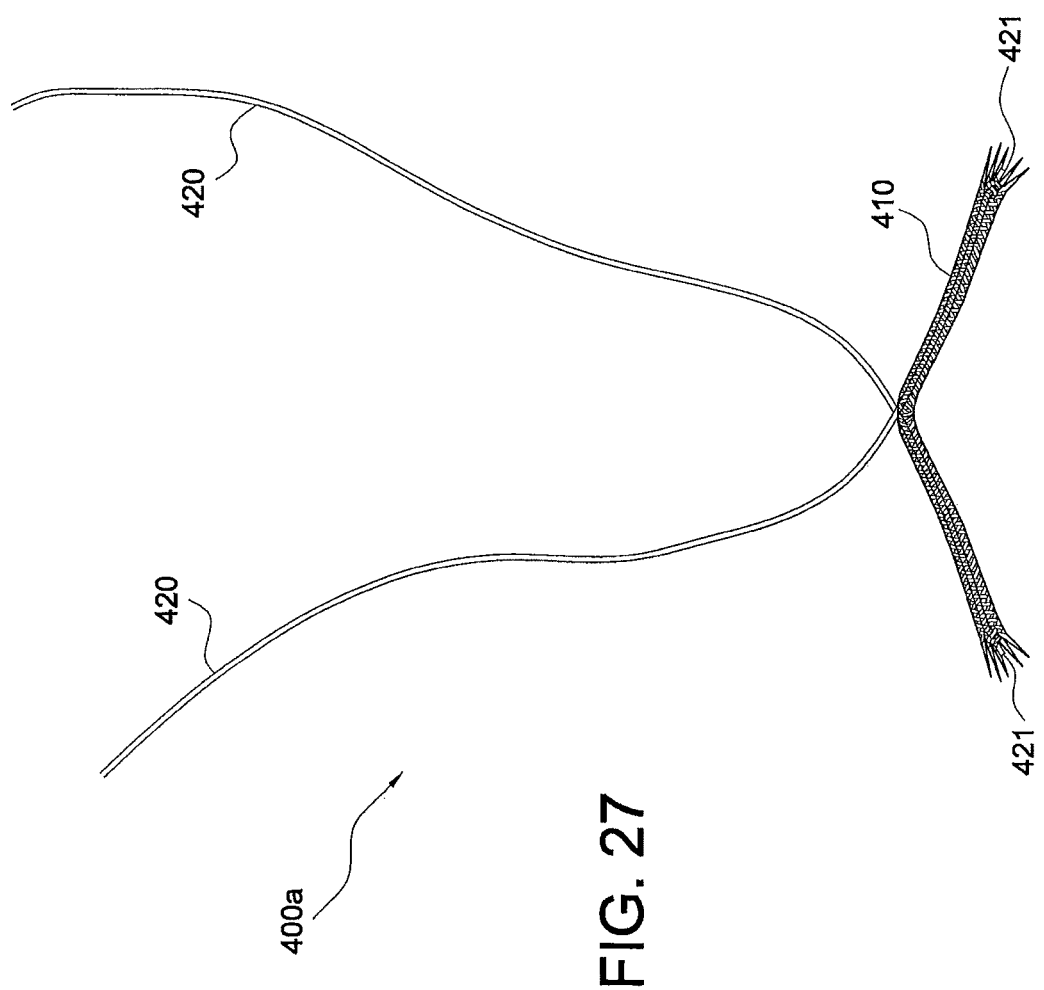
FIG. 27 illustrates another view of the soft anchor implant of FIG. 25.

FIG. 27: Soft anchor implant 400 a (implant A) consists essentially of a continuous piece (strand) of suture tape 410 (FiberTape®️ 410) with a length of approximately 5 cm, of which about 2 cm will be buried into bone on either side of the suture tape. About 1 cm of the suture tape (i.e., the remaining length located in between the 2 cm sides that are buried into bone) acts as a "bridge" over the tissue to be repaired (for example, a torn rotator cuff). The Fiberwire®️ core 420 (preferably a #2 Fiberwire®️ suture) is pulled out the middle of the suture tape 410. A small knot 421 is tied in the end of each core suture 420.

Figure 28:
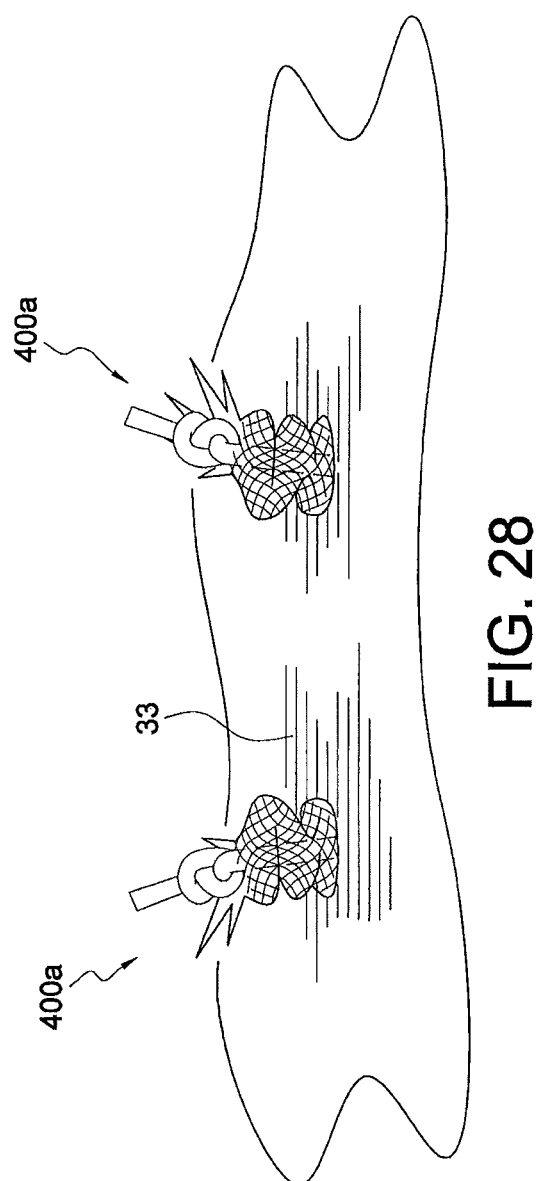
FIGS. 28-33(a) and 33 (b) illustrate methods of tissue fixation with a soft anchor implant of the present invention.

FIG. 28: Each tape end is loaded onto an inserter device 450 (described in more details in FIGS. 40-42) and punched through the tissue (the rotator cuff) and into the bone 33 to a depth of about 2 cm. Each core 420 is then pulled causing the suture tape 410 to become "bunched up" inside the bone, thus securing the implant 400 a inside the bone.

Figure 29:
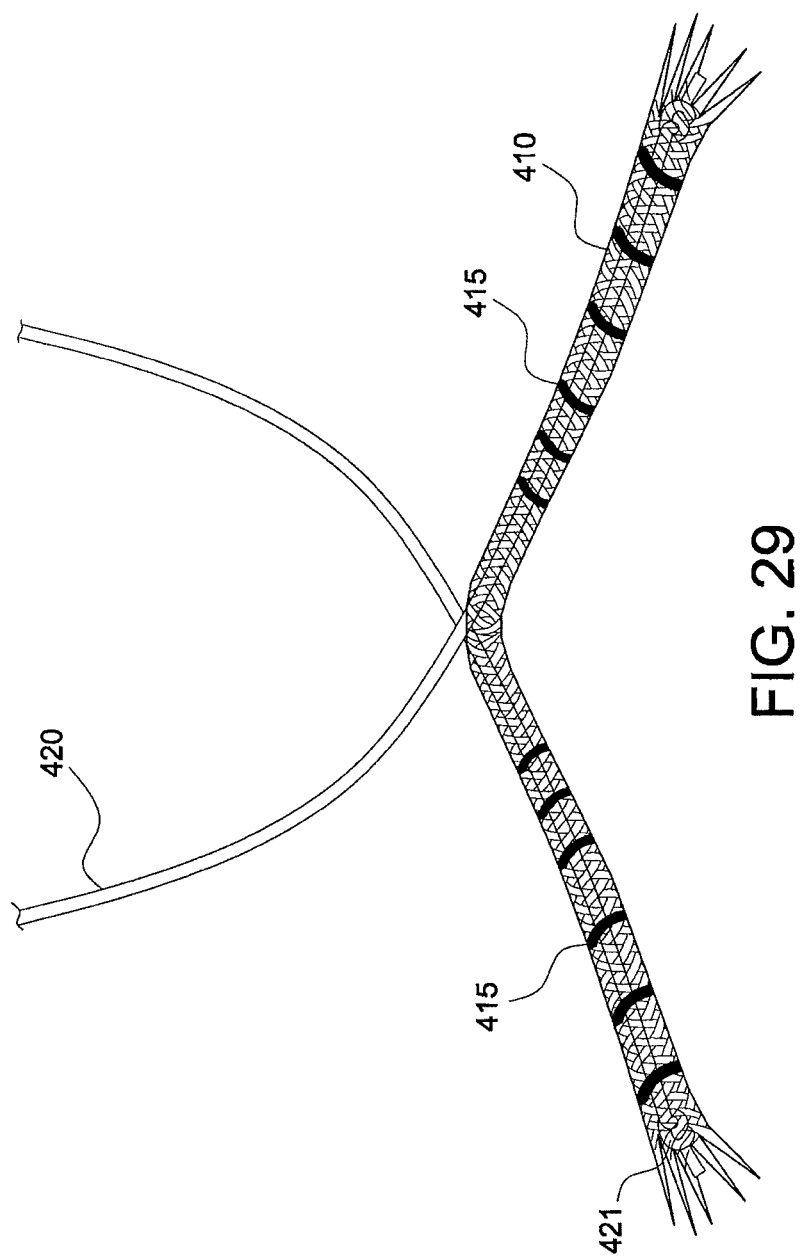

FIG. 29: A marking pen may be employed to mark the 2 cm intermedullary portions 415 of the suture tape 410 of the implant 400 a.

Figure 30:
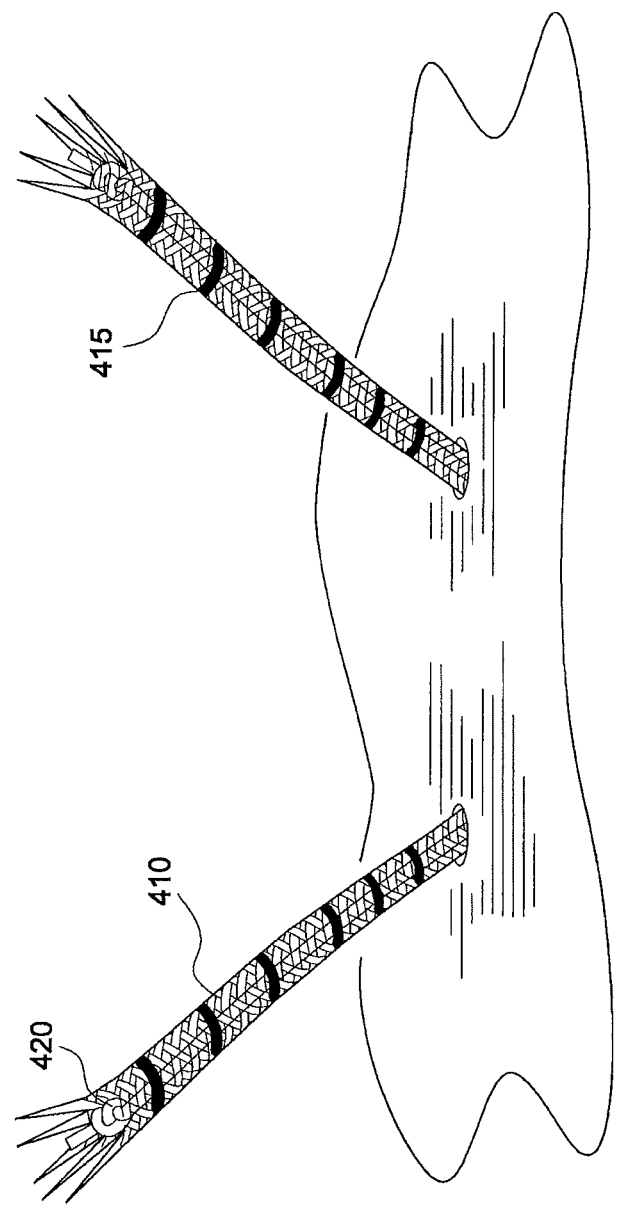

FIG. 30: The implant punctures the tissue (exemplary cardboard) and the 2 cm intermedullary portions 415 of the suture tape 410 are inserted through the tissue (exemplary cardboard).

Figure 31:
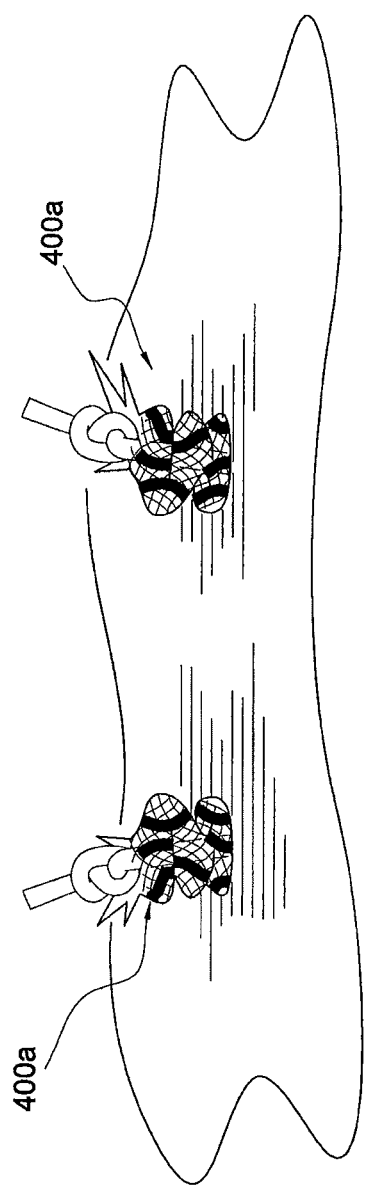

FIG. 31: Pull on the core sutures 420 to deploy the implant 400 a.

Figure 32:
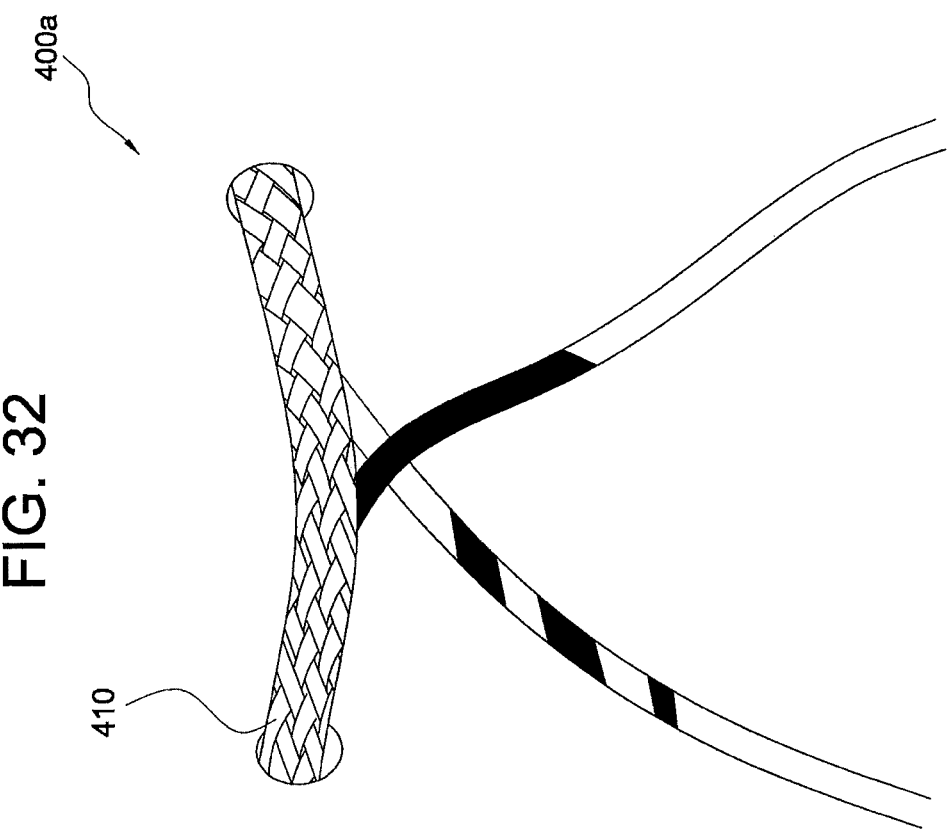

FIG. 32: The implant is seen from the top—the bridge of suture tape 410 extends across the tissue (i.e., the rotator cuff or the exemplary cardboard).

Figure 33A:
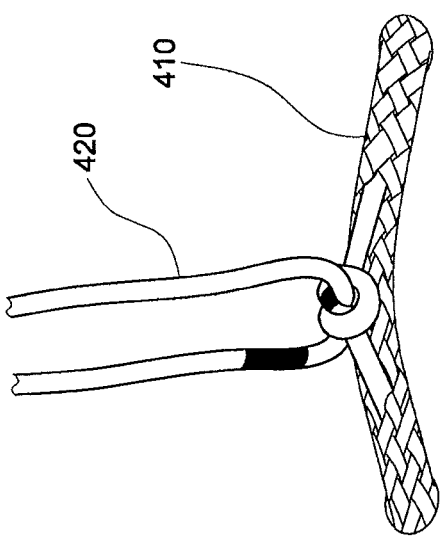
Figure 33B:
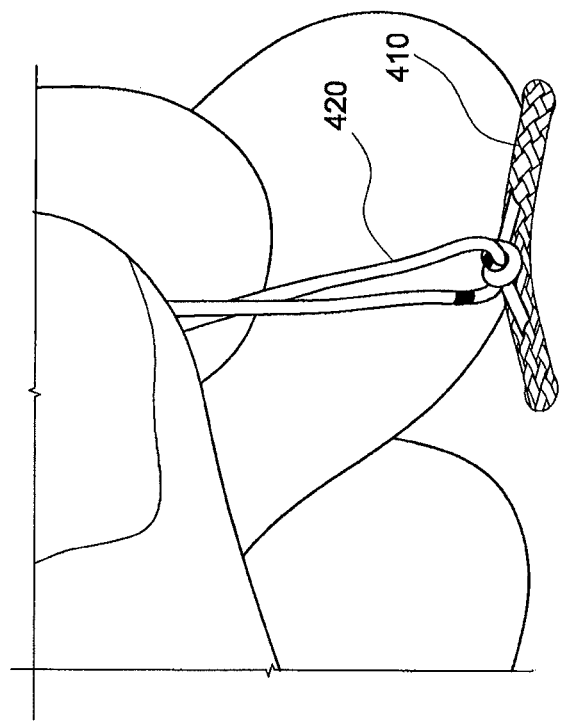

FIGS. 33(a) and (b): The core sutures 420 are tied to one another to secure the bridge of suture tape 410 on top of the tissue (i.e., on top of the rotator cuff or the exemplary cardboard). The anchors are deployed underneath the bridge and the tissue, and the bridge is seen on top of the tissue.

Figure 34:
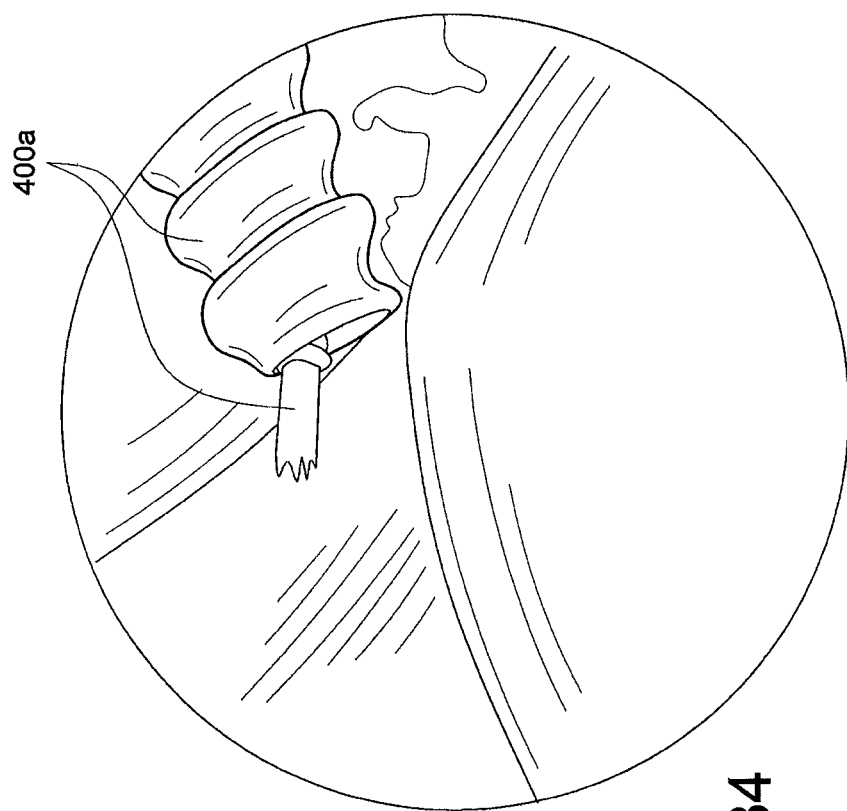
FIGS. 34-41, 42(a), 42(b), and 43-45 illustrate other methods of tissue fixation with soft anchor implants of the present invention.
Figure 35:
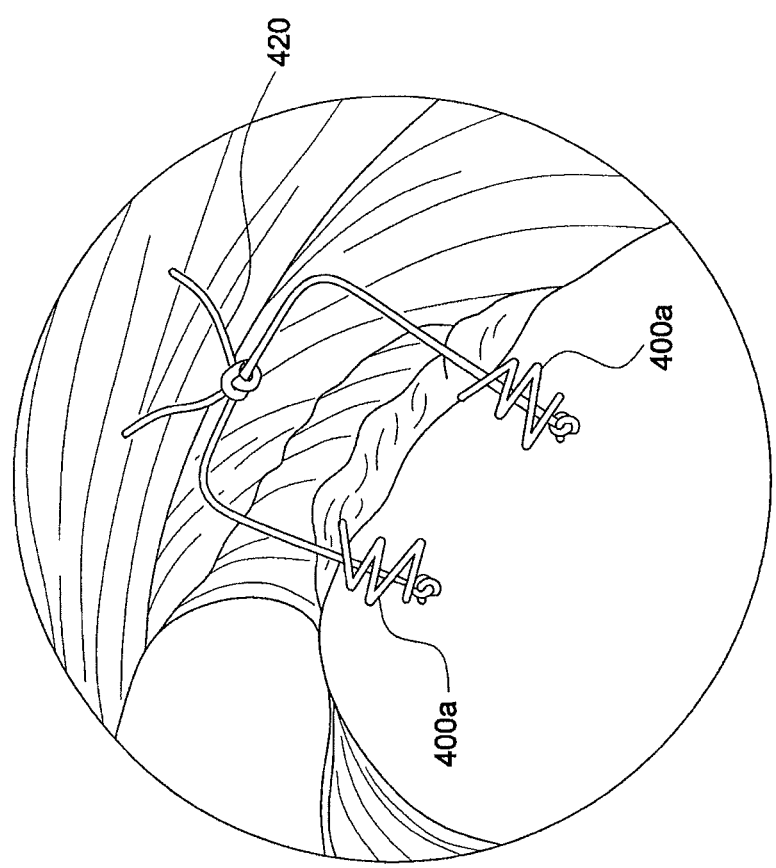

FIGS. 34 and 35 illustrate implant 400 a of the present invention employed in an exemplary tissue repair, i.e., a PASTA repair (Partial Articular-Sided Tendon Avulsion repair), which is typically considered to be a challenging trans-tendon rotator cuff repair that requires passing sutures through the rotator cuff and large implants of about 4.5 to about 5.5 mm. FIG. 35 depicts a PASTA repair with two anchors 400 a of the present invention, for large legions (only one anchor may be used for small lesions).

FIG. 35 illustrates a first anchor 400 a inserted percutaneously through the rotator cuff and down into the bone. Moving over into the subacromial (SA) space, a second anchor 400 a is inserted into the bone by first penetrating the rotator cuff. The second anchor is secured into the bone by pulling on the core suture to deploy the anchor (i.e., to bunch up the suture tape within the tunnel/socket in the bone). The core sutures 420 from the two anchors 400 a are then tied together over the repair and on top of the cuff (to compress the PASTA lesion to the prepared bone bed).

Figure 36:
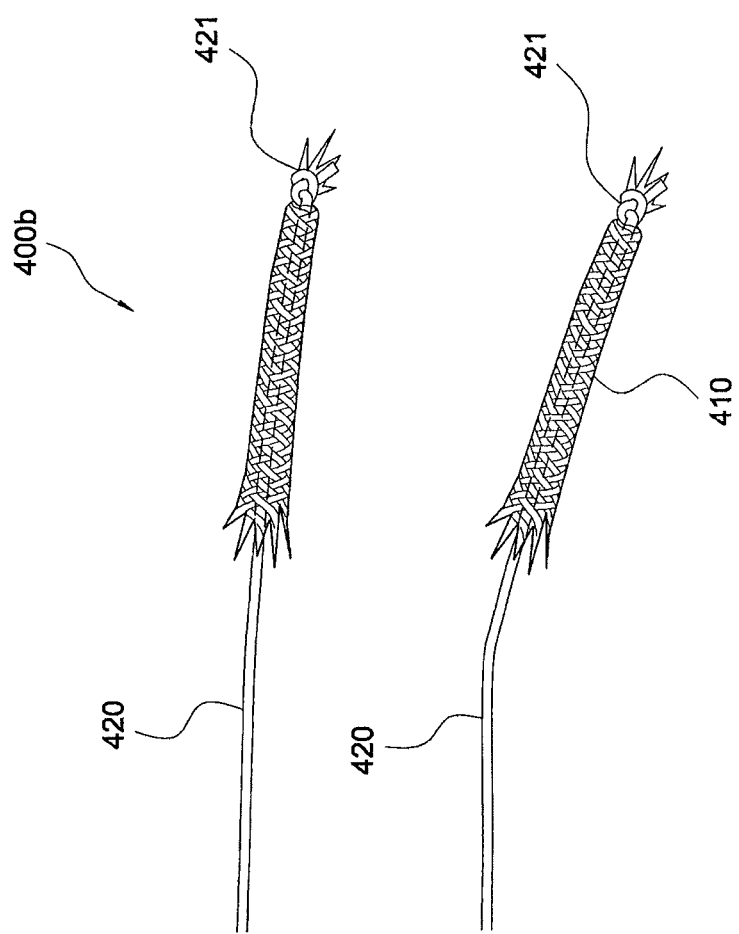
Figure 37:
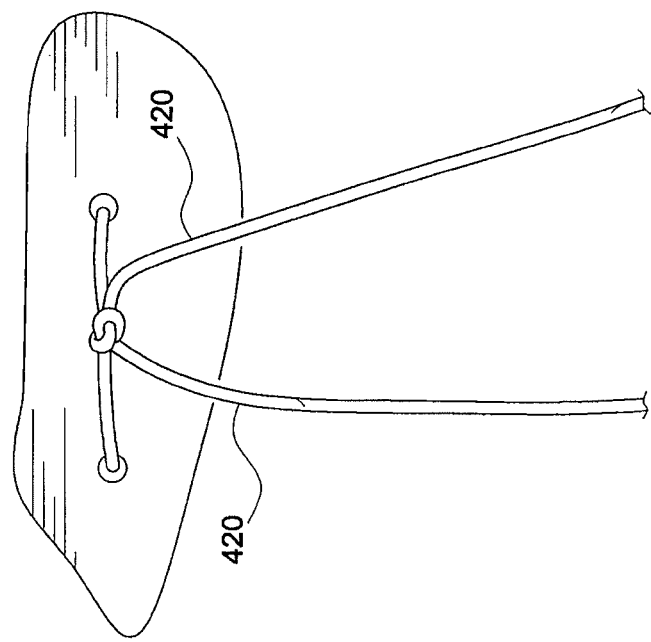
Figure 38:
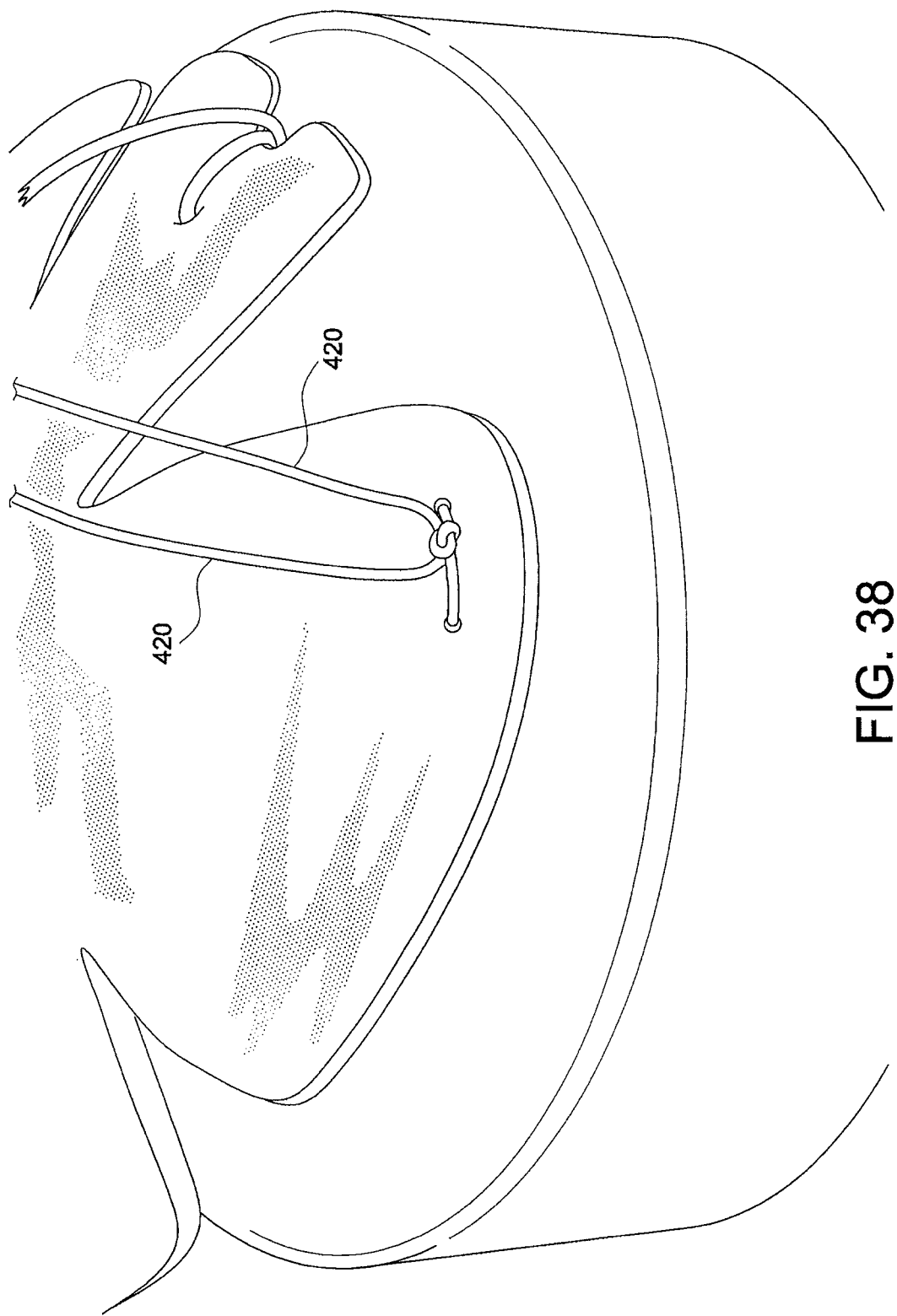

FIGS. 36-38 illustrate implant 400 b of the present invention employed in another exemplary tissue repair according to the present invention. Implant 400 b consists of two separate soft anchors (FiberTape®️ anchors). Each anchor consists essentially of a length of suture tape (a FiberTape®️) 410 of about 2 cm with a suture core (a #2 FiberWire®️ core) 420 extending therethrough. When the anchor is deployed, the 2 cm FiberTape®️ will be buried into bone together with the knot 421 (formed as in implant 400 a). The suture core 420 is used for the repair.

FIGS. 37 and 38 illustrate both anchors of implant 400 b pierced through exemplary tissue (i.e., cardboard and clover leaf). By pulling on the core sutures 420, each of the anchors is deployed into the bone. The core sutures 420 are then tied together on top of the tissue, to secure the construct.

Figure 39:
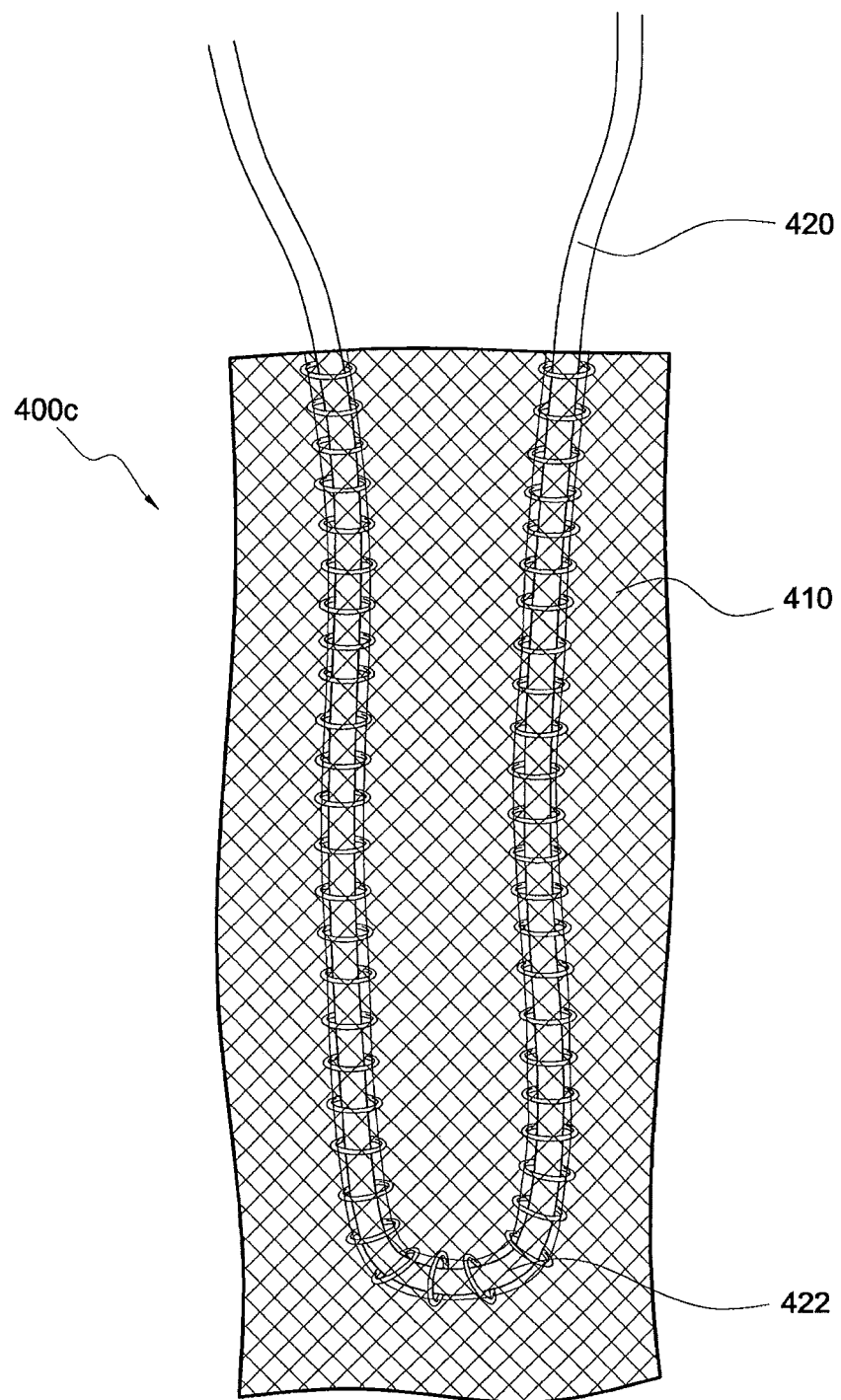

FIG. 39 illustrates implant 400 c which is a modified FiberTape®️ anchor that consists essentially of a length of suture tape (FiberTape®️) 410 of about 2 cm with a suture core 420 (for example, #2 FiberWire®️ core 420) extending therethrough and forming a loop 422 within the body of the suture tape 410 (or securely attached to the outside of the body of the suture tape). Implant 400 c is about similar to implant 400 b but differ in that the core suture 420 is looped into the FiberTape®️ anchor. Each implant 400 c (anchor 400 c) may be about 2 cm in length. When the #2 FiberWire®️ core suture is pulled, the FiberTape®️ anchor bunches up (i.e., deploys or accordionizes). Since no knot is present, the looped core suture can slide within the implant 400 c. The core sutures 420 are used for repair.

The accordion anchors 400 a, 400 b, 400 c detailed above have increased pull-out strength (dramatically stronger compared to the strength of current suture anchors known in the art), and offer the following advantages:

No permanent solid anchor is present;

If implant gets loose, there is no hard abrasive surface to do damage to the surrounding structures;

No bone/anchor cyst reaction;

Easy revision if necessary;

Provides broad area of issue compression via the suture tape;

Allows for scans/MRI—no scatter;

Diminishes the permanent stress riser;

Porous nature of the soft anchors 400 a, 400 b, 400 c allows for vigorous bone ingrowth into the FiberTape®️ anchor pores—the FiberTape®️ may be coated with collagen and/or other tissue growth-promoting compositions and materials such as hyaluronic acid, for example; and Bone marrow contents can easily seep up through the soft anchor into the repair site thus enhancing healing.

Figure 40:
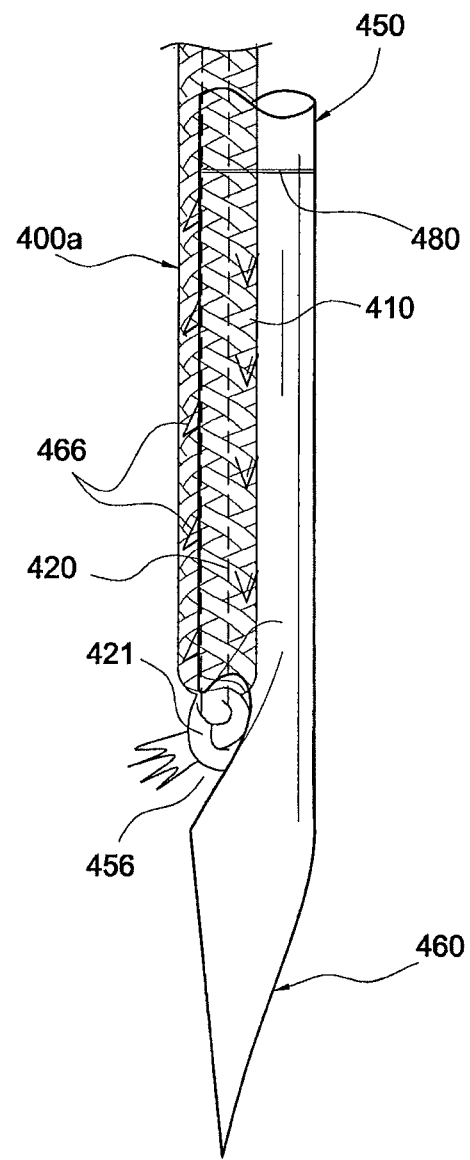
Figure 41:
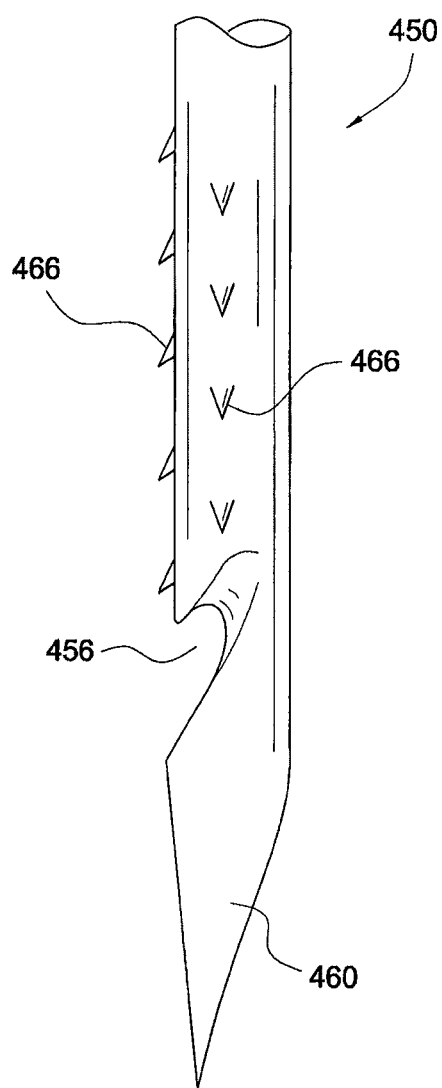
Figure 42A:
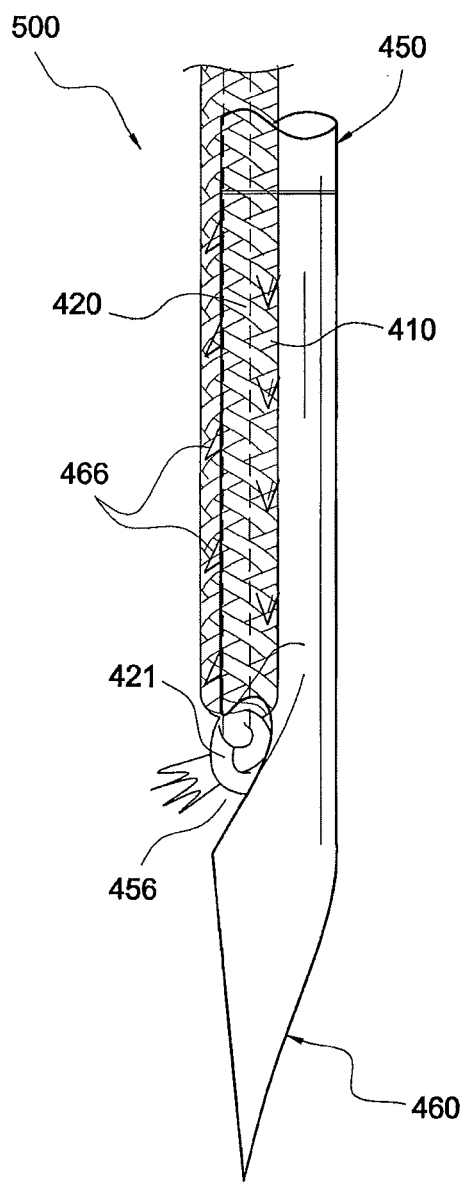
Figure 42B:
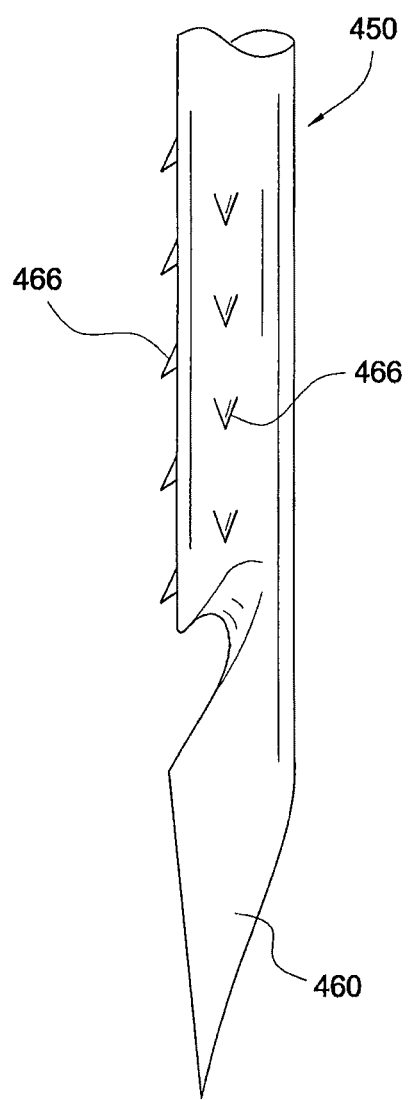

FIGS. 40-42 (a) and (b) illustrate details of an exemplary insertion device 450 which may be used to secure soft suture implants (such as, for example, the soft suture implants 90, 100, 200, 90 a, 400 a, 400 b, 400 c of the present invention). The insertion device 450 may be provided preloaded with an accordion anchor (such as anchor 400 a, for example) or with multiple accordion anchors. The insertion device 450 may have the configuration of a sharp spear with a sharp tip that creates the bone tunnel/socket for anchor insertion. The insertion device 450 may have the shape of a small needle (for example, an 18 gauge needle, or about 1.6 mm) provided with a groove 456 at the neck where the anchor knot 421 fits. In an exemplary embodiment, and as shown in FIG. 40, the anchor wraps circumferentially around the shaft of the inserter 450.

As shown in FIG. 40, spikes 466 on the inserter may point down (i.e., in a direction from top to bottom relative to a longitudinal axis of the device) to push the FiberTape®️ into bone (but without catching and pulling the FiberTape®️ out when the inserter is removed). Core suture knot 421 rests (fits into) the groove 456 in the inserter. The sharp spear tip 460 creates the bone tunnel for anchor insertion. The inserter may be provided with at least one marking line 480 to indicate how far to insert the FiberTape®️. Red markings on the FiberTape®️ may be used to ensure that an appropriate length of the FiberTape®️ has been inserted.

FIGS. 41 and 42 illustrate the insertion device 450 without a preloaded anchor and showing the plurality of downward projecting spikes 466 provided on the inserter body, to allow griping of the suture tape (FiberTape®) of the soft implant during insertion. As the inserter 450 is pulled out, the spikes 466 "let go" of the soft anchor 400 a. Preferably, the spikes 466 are very shallow to avoid creating undo friction during anchor insertion. The design of the spikes mimics how a rasp creates friction in one direction with minimal friction in the opposite direction.

Figure 43:
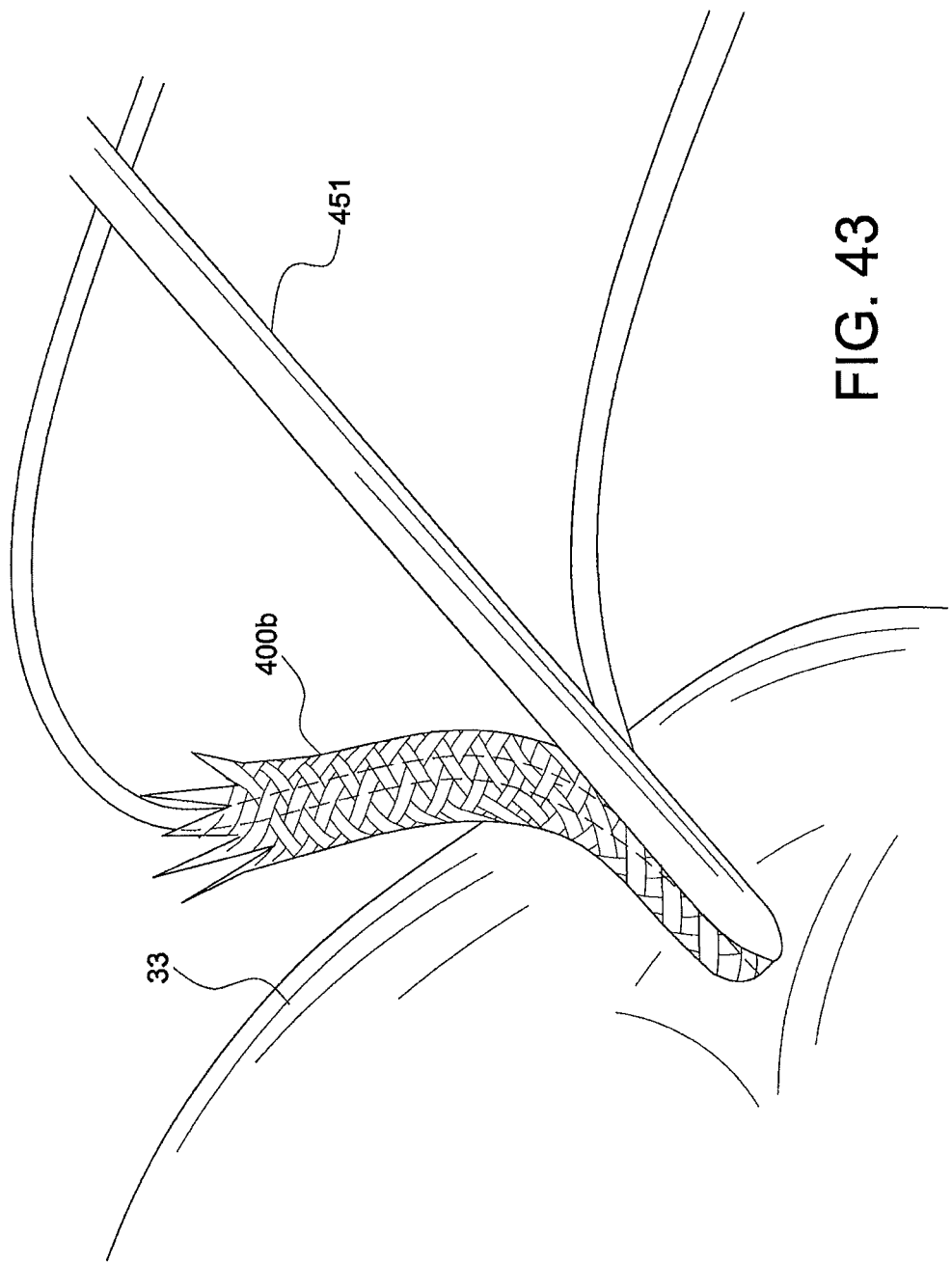
Figure 44:
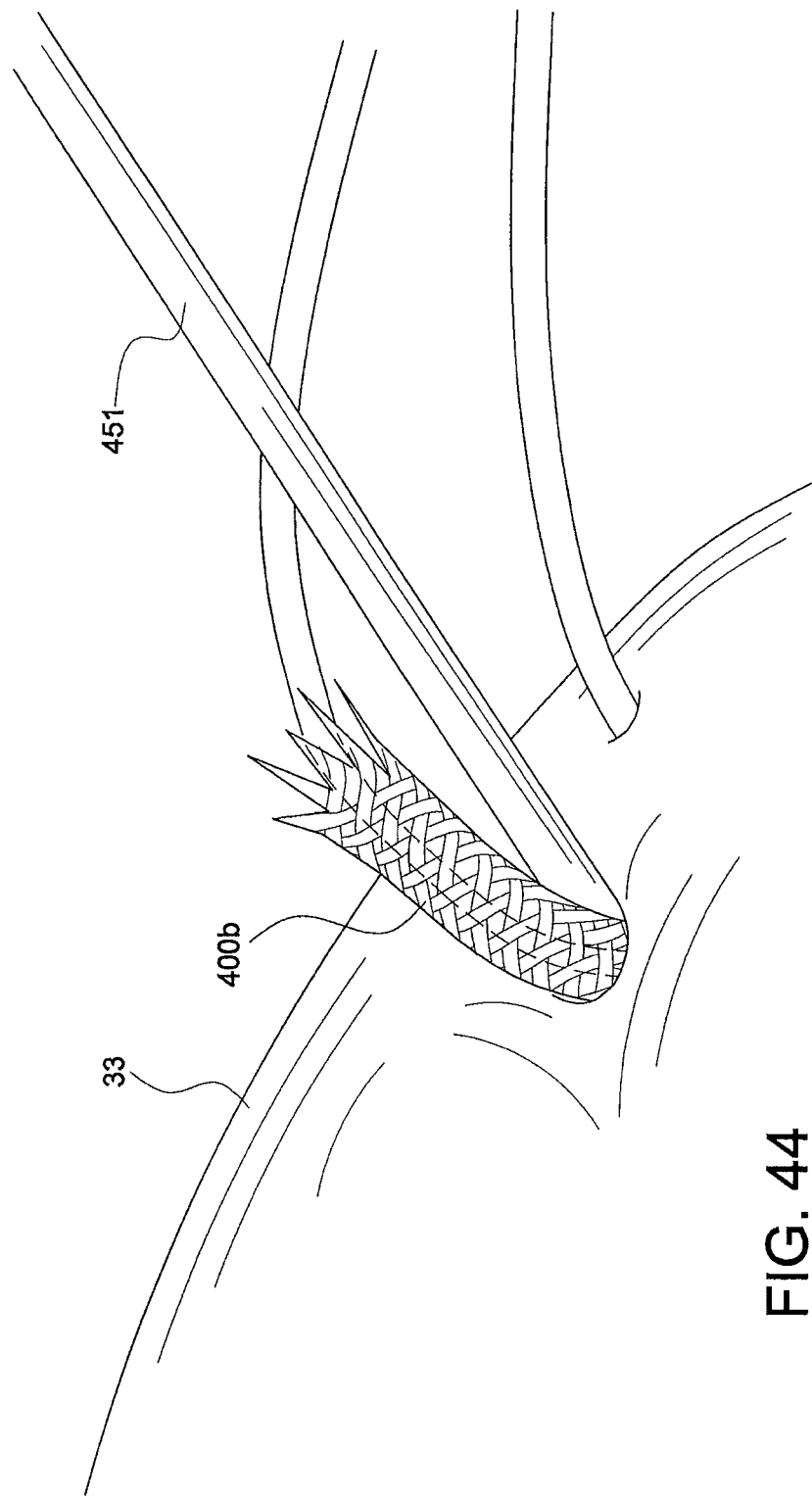

FIGS. 42(a) and (b) illustrate how each anchor could be loaded on a separate insertion spear to obtain anchor/insertion device assembly 500. If multiple insertion devices/spears 450 are used, the spears 450 could be loaded into a gun-type device such as, for example, the Arthrex "Meniscal Cinch" device. For example, FIGS. 43 and 44 illustrate a spear 451 from a meniscal cinch assembly that pushes implant B (anchor 400 b) into the bone.

The accordion anchors 400 a, 400 b, 400 c detailed above may be also employed with a self-cinching suture mechanism that could be incorporated into the implant/anchor. Once the anchor is deployed, the surgeon would simply pull on the self-cinching suture strands to firmly secure the device and compress the tissue (for example, the rotator cuff). The accordion anchors 400 a, 400 b, 400 c could be utilized for multiple additional indications such as, for example, AC joint reconstruction (as shown in FIG. 45, wherein the #2 FiberWire® core sutures are passed through the coracoid and clavicle and then tied over a button having a dog-bone configuration), syndesmosis reconstruction, quad/patellar tendon rupture repair, hallux-valgus repair, and any other tendon repair to bone.

Figure 45:
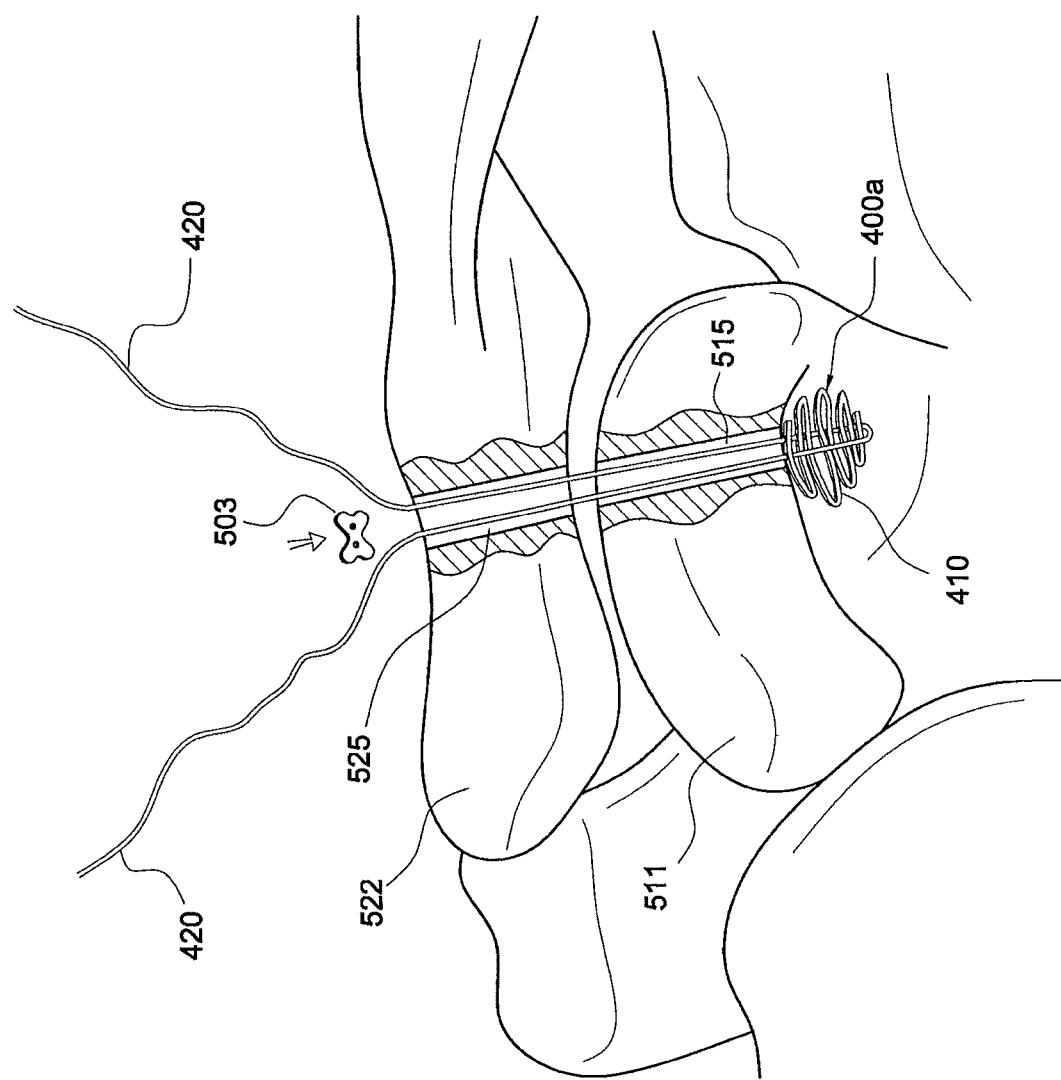

As shown in FIG. 45, the accordion anchor 400 a (the FiberTape® anchor) is employed in an exemplary AC joint reconstruction method with a fixation device 503 (button 503) having a specific "dog-bone-shape" configuration, as detailed and described in U.S. Patent Application Publication No. 2012/0150203, the disclosure of which is incorporated by reference in its entirety herewith. The #2 FiberWire® core sutures 420 are passed through tunnels 515, 525 in the coracoid 511 and clavicle 522 (for example, small 2 mm tunnels), and then tied over the dog-bone button 503, to accordionize the tape and form the accordion anchor at the base of the coracoid.

The accordion anchors 400 a, 400 b, 400 c detailed above may be also employed in conjunction with additional various knotted and/or knotless fixation devices (or combination of such knotted and knotless fixation devices), such as PushLock® anchors and/or SwiveLock® anchors to secure, for example, a medial row on rotator cuff repairs.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A surgical system, comprising:
   an inserter; and
   a suture based anchor received against an outer surface of the inserter,
   wherein the suture based anchor includes a unitary first flexible suture strand and a separate second flexible suture strand that passes through an internal portion of the first flexible suture strand at three or more distinct locations; wherein a first location of the three or more distinct locations is spaced a first distance from a second location of the three or more distinct locations, and a third location of the three or more distinct locations is spaced a second distance from the second location, and further wherein the first distance and the second distance are equal distances.

2. The surgical system as recited in claim 1, wherein the outer surface includes a forked tip, and the suture based anchor is looped over the forked tip.

3. The surgical system as recited in claim 1, wherein the suture based anchor is made exclusively of suture-based materials.

4. The surgical system as recited in claim 1, wherein the second flexible suture strand passes through the first flexible suture strand at four or more distinct locations.

5. The surgical system as recited in claim 1, wherein the first and second flexible suture strands each includes braided ultrahigh molecular weight polyethylene (UHMWPE) fibers.

6. The surgical system as recited in claim 1, wherein the first flexible suture strand includes polyester fibers and the second flexible suture strand includes ultrahigh molecular weight polyethylene (UHMWPE) fibers.

7. The surgical system as recited in claim 1, wherein the suture based anchor is configured to move from a first, extended position to a second, compressed position in response to tensioning the second flexible suture strand.

8. The surgical system as recited in claim 1, wherein a first width of the first flexible suture strand is larger than a second width of the second flexible suture strand.

9. The surgical system as recited in claim 1, wherein the suture based anchor extends along a first side of the outer surface, through a slot formed in the outer surface, and along a second side of the outer surface.

10. The surgical system as recited in claim 1, wherein the first flexible suture strand and the second flexible suture strand are colored differently.

11. The surgical system as recited in claim 1, wherein the second flexible suture strand forms a loop within a body of the first flexible suture strand or that extends along an outside of a body of the first flexible suture strand.

12. The surgical system as recited in claim 1, wherein the internal portion includes a core of the first flexible suture strand.

13. The surgical system as recited in claim 1, wherein the second flexible suture strand passes through the internal portion of the first flexible suture strand to establish a suture-through-suture configuration at the three or more distinct locations.

14. A surgical system, comprising:
   a suture based anchor comprised exclusively of suture-based materials including a unitary first flexible suture strand and a separate second flexible suture strand passed through a core of the first flexible suture strand at three or more distinct locations,
   wherein the first flexible suture strand includes polyester fibers,
   wherein the second flexible suture strand includes ultra-high molecular weight polyethylene (UHMWPE) fibers;
   wherein the second flexible suture strand passes through the core of the first flexible suture strand to establish a suture through suture configuration at the three or more distinct locations.

15. The surgical system as recited in claim 14, wherein the suture based anchor is looped over a forked tip of an inserter.

16. The surgical system as recited in claim 14, wherein the suture based anchor further includes a third flexible suture strand passed through the first flexible suture strand at each of the three or more distinct locations to provide a double-loaded suture based anchor, and wherein the third flexible strand includes ultrahigh molecular weight polyethylene (UHMWPE) fibers.

17. The surgical system as recited in claim 14, wherein the second flexible suture strand passes through the first flexible suture strand at six or more distinct locations.

* * * * *